United States Patent
Schueler et al.

(10) Patent No.: US 7,399,963 B2
(45) Date of Patent: Jul. 15, 2008

(54) PHOTOELECTRON SPECTROSCOPY APPARATUS AND METHOD OF USE

(75) Inventors: Bruno W. Schueler, San Jose, CA (US); David A. Reed, Belmont, CA (US)

(73) Assignee: ReVera Incorporated, Sunnyvale, CA (US)

( * ) Notice: Subject to any disclaimer, the term of this patent is extended or adjusted under 35 U.S.C. 154(b) by 280 days.

(21) Appl. No.: 11/237,041

(22) Filed: Sep. 27, 2005

(65) Prior Publication Data

US 2007/0069125 A1    Mar. 29, 2007

(51) Int. Cl.
*H01J 40/00* (2006.01)
(52) U.S. Cl. .................................. 250/305; 250/526
(58) Field of Classification Search .................. 250/305
See application file for complete search history.

(56) References Cited

U.S. PATENT DOCUMENTS

| | | | |
|---|---|---|---|
| 4,486,659 A | 12/1984 | Turner | |
| 5,053,625 A | 10/1991 | Follett | |
| 6,545,272 B1* | 4/2003 | Kondo | 250/305 |
| 6,586,728 B1* | 7/2003 | Gavin et al. | 250/287 |
| 6,873,915 B2* | 3/2005 | Hastings | 702/22 |
| 2004/0135081 A1* | 7/2004 | Larson et al. | 250/305 |
| 2006/0190916 A1* | 8/2006 | Pike | 716/21 |

OTHER PUBLICATIONS

PCT International Search Report for Application No. PCT/US 06/34781, mailing date Sep. 24, 2007 (5 pages).
PCT International Written Opinion for Application No. PCT/US 06/34781, mailing date Sep. 24, 2007 (5 pages).

* cited by examiner

*Primary Examiner*—Jack I. Berman
*Assistant Examiner*—Andrew Smyth
(74) *Attorney, Agent, or Firm*—Blakely, Sokoloff, Taylor & Zafman LLP

(57) ABSTRACT

According to one aspect of the present invention, a substrate processing system is provided. The system may include a chamber wall enclosing a chamber, a substrate support positioned within the chamber to support a substrate, an electromagnetic radiation source to emit electromagnetic radiation onto the substrate on the substrate support, the electromagnetic radiation causing photoelectrons to be emitted from a material on the substrate, an analyzer to capture the photoelectrons emitted from the substrate, and a magnetic field generator to generate a magnetic field within the chamber and guide the photoelectrons from the substrate to the analyzer.

65 Claims, 21 Drawing Sheets

PHOTOELECTRON SPECTROSCOPY APPARATUS AND METHOD OF USE

BACKGROUND OF THE INVENTION

1). Field of the Invention

The present invention relates to a method, apparatus, and system for processing semiconductor substrates, particularly to a metrology tool for use in processing semiconductor substrates.

2). Discussion of Related Art

Integrated circuits are formed on semiconductor substrates such as wafers. The formation of the integrated circuits may include numerous processing steps such as deposition of various layers, etching some of the layers, and multiple bakes. The integrated circuits are then separated into individual microelectronic dice, which are packaged and attached to circuit boards.

During the various processing steps involved in the creation of the integrated circuits, various layers of different materials, such as conductors, dielectrics, and semiconductor, are formed on the surface of the wafer where the integrated circuits are being formed. The manufacturers of the integrated circuits often test the composition of the various layers to ensure that the proper materials are being deposited on the substrates.

The machines used to test the composition of the layers are often referred to as "metrology tools." The metrology tools emit electromagnetic radiation, such as x-rays from an x-ray source, which are directed to a particular region of a substrate that is being tested. The metrology tools make use of analysis techniques, such as X-ray Photoelectron Spectroscopy (XPS), Total Reflection X-ray Fluorescence (TXRF), and ellipsometry, to measure particular characteristics of the substrate. If, for example, XPS is used, photoelectrons, or electrons, are emitted from the substrate and captured by a metrological analyzer, such as an electron spectrometer or hemispherical analyzer. The analyzer and associated processing algorithms determine the composition of the region of the substrate by analyzing the kinetic energy, or speed, of the photoelectrons.

In order to properly position the substrates, specifically the pads on the substrates, relative to the electromagnetic radiation source, vision systems may be used which utilize pattern recognition software.

However, typically the vision systems are only able to view the pads at an angle, so the image is not ideal. Additionally, the systems are not able to view a particular pad while it is being tested. Furthermore, the vision systems typically include multiple actuators and other moving parts, which create contaminates within the tool.

Often, magnetic field generators, or magnetic lenses, are used to guide the photoelectrons from the substrate into the analyzers. However, the metrology tools usually include both a robot to transport the substrates into the tool, and a separate stage to hold the substrates under the analyzer and above the magnetic lens. The separate stage occupies a considerable amount of space within the tool, and the magnetic lenses must be located below the stage, which detrimentally affects the effectiveness of the magnetic lens.

Furthermore, the contents of the metrology tools, including the magnetic lens, are typically held within vacuum chambers. If the magnetic lens requires any sort of maintenance, the vacuum must be broken, which increases the likelihood that the interior of the tool will be contaminated.

One common example of an electromagnetic radiation source that is used in the metrology tools is the combination of an electron gun, anode, and a monochromator. The electron gun fires electrons onto a relatively small target portion of the anode, and x-rays are emitted from the anode onto the monochromator, which deflects and focuses the x-rays onto the substrate.

SUMMARY OF THE INVENTION

Embodiments of the present invention provide a substrate processing system. The system may include a chamber enclosed by a chamber wall, a substrate or specimen support positioned within the chamber to support a substrate or specimen, an electromagnetic radiation source to emit electromagnetic radiation onto the substrate on the substrate support, the electromagnetic radiation causing photoelectrons to be emitted from the substrate surface, an analyzer to capture the photoelectrons emitted from the material on the semiconductor substrate, and a magnetic field generator to generate a magnetic field within the chamber and guide the photoelectrons from the substrate to the analyzer. In an embodiment of the present invention, the substrate or specimen support, electromagnetic radiation source, analyzer and magnetic field generator are each connected to the chamber wall.

Embodiment of the present invention also provide a substrate processing system which may include a chamber wall enclosing a vacuum chamber, a substrate or specimen support positioned within the vacuum chamber to support a substrate, an electromagnetic radiation source to emit electromagnetic radiation onto the substrate on the substrate support, the electromagnetic radiation causing photoelectrons to be emitted from the substrate, an analyzer to capture the photoelectrons emitted from the substrate, and a magnetic field generator to generate a magnetic field within the vacuum chamber and guide the photoelectrons from the semiconductor substrate to the analyzer, the magnetic field generator being positioned outside of the vacuum chamber.

The invention also provides a semiconductor substrate processing apparatus which may include a chamber wall enclosing a chamber having a loading portion and a testing portion, a robotic stage having a robotic arm connected to the chamber wall and a substrate or specimen support attached to the robotic arm, the robotic arm being capable of moving the substrate support between the loading and test portions of the chamber, an electromagnetic radiation source to emit electromagnetic radiation onto a substrate on the substrate support when the substrate support is in the testing portion of the chamber, the electromagnetic radiation causing photoelectrons to be emitted from the substrate, an analyzer to capture the photoelectrons emitted from the substrate, and a magnetic field generator to generate a magnetic field within the chamber and guide the photoelectrons from the substrate to the analyzer, the magnetic field generator being positioned beneath the substrate support when the substrate support is in the testing portion of the chamber.

Embodiments of the present invention further provide a substrate processing apparatus which may include a chamber wall enclosing a chamber, a substrate support positioned within the chamber to support a semiconductor substrate, an electromagnetic radiation source to emit electromagnetic radiation onto a portion of the substrate on the substrate support, the electromagnetic radiation causing photoelectrons to be emitted from the portion of the substrate, an analyzer to capture the photoelectrons emitted from the material on the portion of the substrate, and a camera subsystem connected to the chamber wall to collect visible light that is reflected off the portion of the substrate and capture an image of the portion of the semiconductor substrate.

Embodiments of the present invention further provide a substrate processing apparatus which may include a chamber wall enclosing a chamber, a substrate support positioned within the chamber to support a substrate, an electromagnetic radiation source connected to emit electromagnetic radiation onto a portion of the substrate on the substrate support, the electromagnetic radiation causing photoelectrons to be emitted from a material on the portion of the substrate, an analyzer connected to the chamber wall to capture the photoelectrons emitted from the material on the portion of the substrate, a magnetic field generator to generate a magnetic field within the chamber and guide the photoelectrons from the substrate to the analyzer, and a camera subsystem to collect visible light that is reflected off the portion of the substrate and capture an image of the portion of the semiconductor substrate.

Embodiments of the present invention further provide a substrate processing apparatus which may include a substrate support to support a substrate having an upper surface, and a camera subsystem to collect visible light that is reflected off a portion of the substrate and capture an image of the portion of the substrate, the visible light propagating from the portion of the substrate in a direction that is substantially perpendicular to the upper surface of the substrate surface.

Embodiments of the present invention further provide a substrate processing apparatus which may include a chamber wall enclosing a chamber, a substrate support positioned within the chamber to support a substrate, an electromagnetic radiation source connected to emit a beam of electromagnetic radiation onto a portion of the substrate, the electromagnetic radiation causing photoelectrons to be emitted from the portion of the semiconductor substrate and an analyzer connected to capture the photoelectrons emitted from the material on the substrate.

In an embodiment of the present invention the electromagnetic radiation source includes an electron source for providing an electron beam for irradiating an anode with electrons to produce electromagnetic radiation, such as X-rays, and a monochromator to focus the emitted electromagnetic radiation onto the substrate or specimen. In embodiments of the present invention, the electron source includes shaping means, such as an octopole or aperture shutters to shape the electron beam into a desired shape or profile. The electron beam can be shaped into a desired profile, such as but not limited to a circle, an elongated oval, a square, and a rectangle. In an embodiment of the present invention, an electron beam is shaped into an elongated oval or rectangle having a length is 1-3 times larger than its width. Additionally, in an embodiment of the present invention, a large area monochromator with a large solid angle is utilized to increase the collection efficiency of the monochromator. A large area monochromator with a large solid angle enables the e-beam shape to be transferred into an X-ray profile pattern which is highly correlated to the e-beam shape on the anode.

BRIEF DESCRIPTION OF THE DRAWINGS

The invention is described by way of example with reference to the accompanying drawings, wherein.

DETAILED DESCRIPTION OF THE INVENTION

In the following description, various aspects of the present invention will be described, and various details set forth in order to provide a thorough understanding of the present invention. However, it will be apparent to those skilled in the art that the present invention may be practiced with only some or all of the aspects of the present invention, and the present invention may be practiced without the specific details. In other instances, well-known features are omitted or simplified in order not to obscure the present invention.

It should be understood the FIGS. 1A through 10C are merely illustrative and may not be drawn to scale.

An embodiment of the present invention provides what is known in the art as a "metrology tool." The metrology tool may include load-lock chamber and a metrology chamber, enclosing a vacuum chamber, with a loading portion and a testing portion. A robotic stage may be located within loading portion of the metrology chamber to transport semiconductor substrates from the load-lock chamber to the testing portion of the metrology chamber. The metrology tool may also include a magnetic lens positioned below the testing portion of the metrology chamber and outside the vacuum chamber.

The metrology tool may also include an electromagnetic radiation source capable of emitting a beam of electromagnetic radiation onto features on the substrates in particular shapes and sizes. Additionally, the metrology tool may include a viewing, or camera, subsystem capable of viewing the features on the substrates at an angle normal (i.e., perpendicular) to the substrates while the electromagnetic radiation is being directed onto the features.

The metrology tool may also include an analyzer to capture and analyze photoelectrons emitted from the features to determine the composition of the features.

Figure 1A:
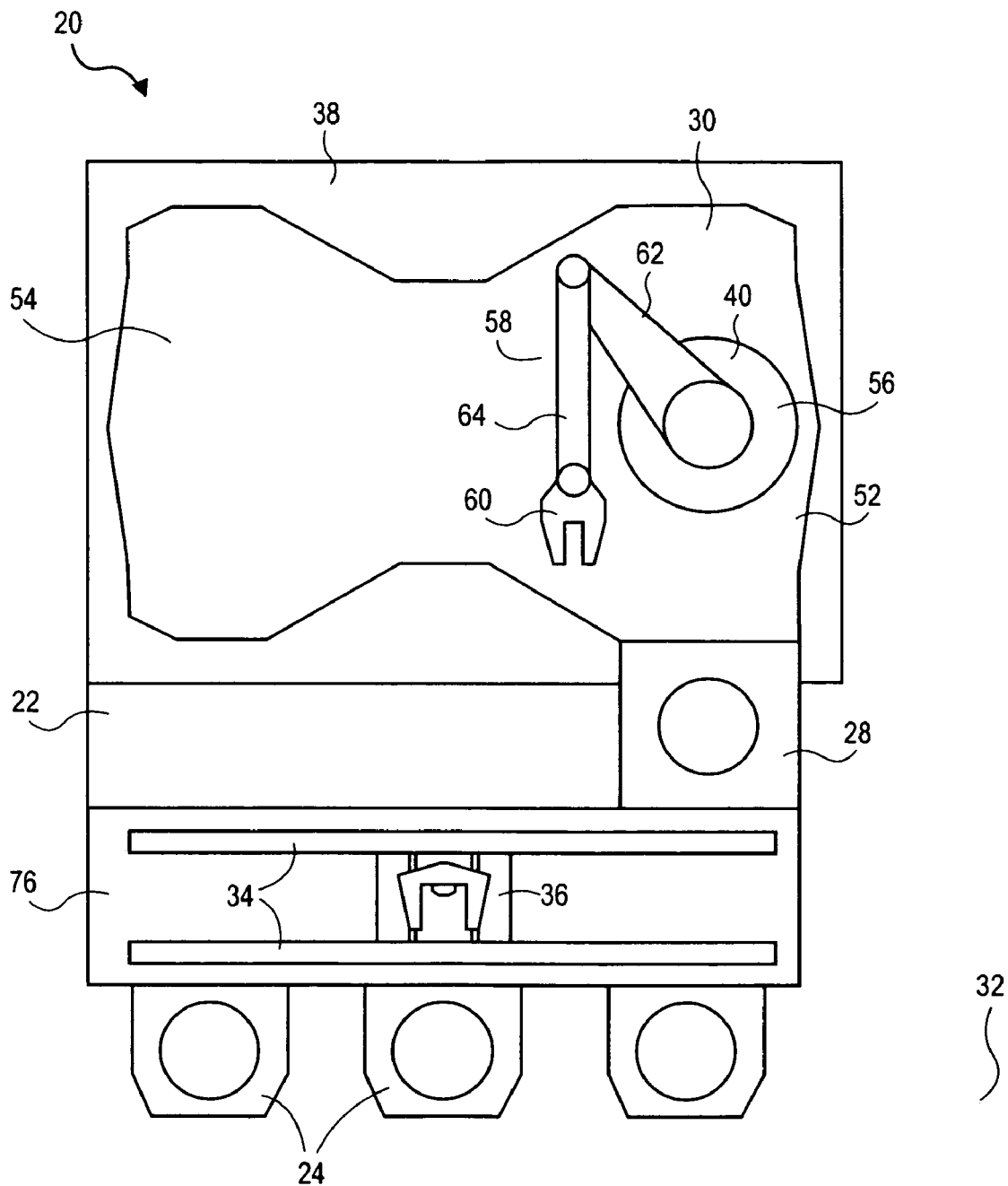
FIG. 1A is top plan schematic view of a semiconductor substrate processing apparatus including a metrology chamber.

FIG. 1A illustrates a substrate processing system, or a metrology tool 20, according to an embodiment of the present invention. The metrology tool 20 may include a frame 22, wafer cassettes 24, a transport subsystem 26, a load-lock chamber 28, a metrology chamber 30 enclosed by a chamber wall 38, and a computer control console 32. The frame 22 may be substantially square with the wafer cassettes 14 attached at a first end thereof. The transport subsystem 26 may lie adjacent to the cassettes 24.

The wafer cassettes 24 may lie at one end of the frame 22 and may be Front Opening Unified Pods (FOUPs), as is commonly understood in the art. The cassettes 24 may be sized and shaped to hold a plurality of semiconductor substrates, such as wafers, with diameters of, for example, 200 or 300 millimeters.

The transport subsystem 26 may include a transport track 34 and a transport mechanism 36. The transport track 34 may be connected to the frame 22 and extend between opposing sides of the frame 22 near the wafer cassettes 24. The transport mechanism 36 may be able to support semiconductor substrates, such as wafers with diameters of, for example, 200 or 300 millimeters and transport the substrates between each of the cassettes 24 and the load-lock chamber 28.

The load-lock chamber 28 may be connected to the frame 22 between the transport subsystem 26 and the metrology chamber 30. As is commonly understood in the art, the load-lock chamber 28 may include a first door adjacent to the transport subsystem 26 and a second door adjacent to the metrology chamber 30. Both doors may be able to hermetically seal the transport subsystem 26 from the metrology chamber 30.

Figure 1B:
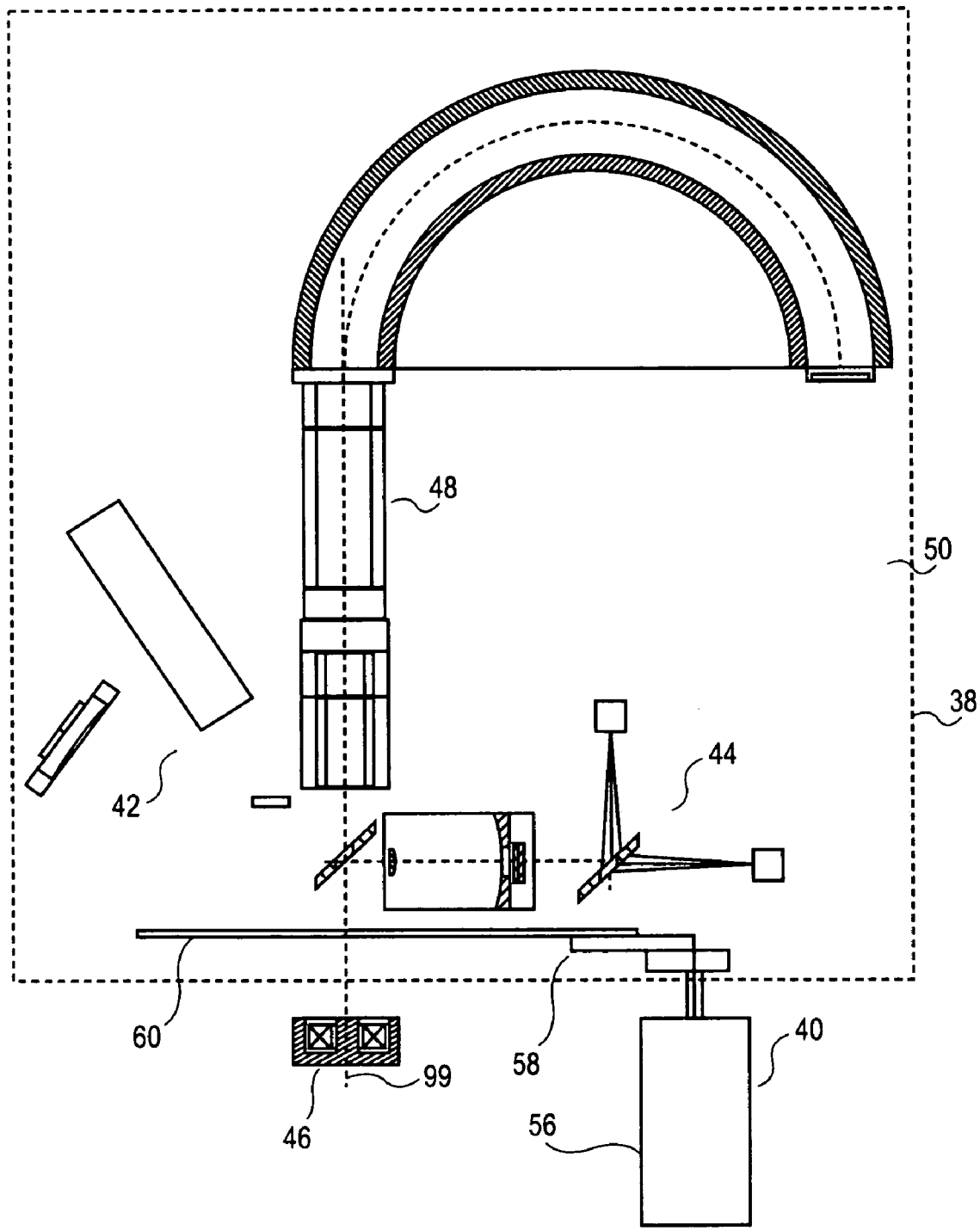
FIGS. 1B, 1C, and 1D are cross-sectional side schematic views of the metrology chamber shown in FIG. 1.

Referring to FIG. 1A in combination with FIG. 1B, the metrology chamber 30, a robotic stage 40, an electromagnetic radiation source subsystem 42, a viewing, or camera, subsystem 44, a magnetic lens 46, and a metrological analyzer 48. The chamber wall 38 may have an inner surface which, when viewed from above, has an "hourglass" shape as illustrated in FIG. 1A. The inner surface of the chamber wall 38 may divide the metrology chamber 30 into first 52 and second 54 portions. As shown, the first portion 52 may be located nearer to the load-lock chamber 28 than the second portion 54. The metrology chamber 30 may also be hermetically sealed to form a vacuum chamber 50 as shown schematically in FIG. 1B.

The robotic stage 40 may lie within the first portion 52 of the metrology chamber 30 and be directly connected to chamber wall 38. The robotic stage 40 may include a base 56, a robotic arm 58, and a substrate support 60. The robotic arm 58 may be rotatably connected to the base 56 and include a first segment 62 attached directly to the base 56 and a second segment 64 attached to an end of the first segment 62. The substrate support 60, or "blade," may be connected to the second segment 64 of the robotic arm 58 at an end opposing the first segment 62. As dictated by the structure of the robotic arm 58, the robotic arm 58 may be able to move the substrate support 60 in a polar coordinate system (R, θ) with at least one axis of rotation extending through the first portion 52 of the metrology chamber 30. Additionally, the robotic arm 58 may be able to move the substrate support 60 vertically (z-motion) within the metrology chamber 30. The substrate support 60 may be sized and shaped to support substrates, such as semiconductor wafers, with diameters of, for example, 200 or 300 millimeters. The robotic stage 40 may be able to extend the substrate support 60 into the second portion 65 of the metrology chamber 30, as well as into the load-lock chamber 28.

It should be noted that because of the position of the base 56 of the robotic stage 40 (i.e., within the first portion 52 of the metrology chamber 30), when the robotic arm 58 extends the substrate support 60 into the second portion 54 of the metrology chamber 30, none of the components of the robotic stage 40 are located below the substrate support 60.

As shown specifically in FIG. 1B, all of the components within the metrology chamber 30 may be located within the vacuum chamber 50, except for the base 56 of the robotic stage 40 and the magnetic lens 46, which both may be positioned below the vacuum chamber 50.

Still referring to FIG. 1B, although not illustrated in detail, the magnetic lens 46, or magnetic field generator, may be connected to the chamber wall 38 and positioned below the second portion 54 of the metrology chamber 30. The magnetic lens is utilized to focus electrons emitted from the substrate or specimen into an analyzer 48. The magnetic lens produces a magnetic field, which has rotational symmetry about central axis 99. The magnetic lens 46 may include a coil and be capable of generating a magnetic field within the metrology chamber 30. In an embodiment of the present invention, the magnetic lens is a single pole piece lens sometimes referred to as a "snorkel lens".

Figure 1C:
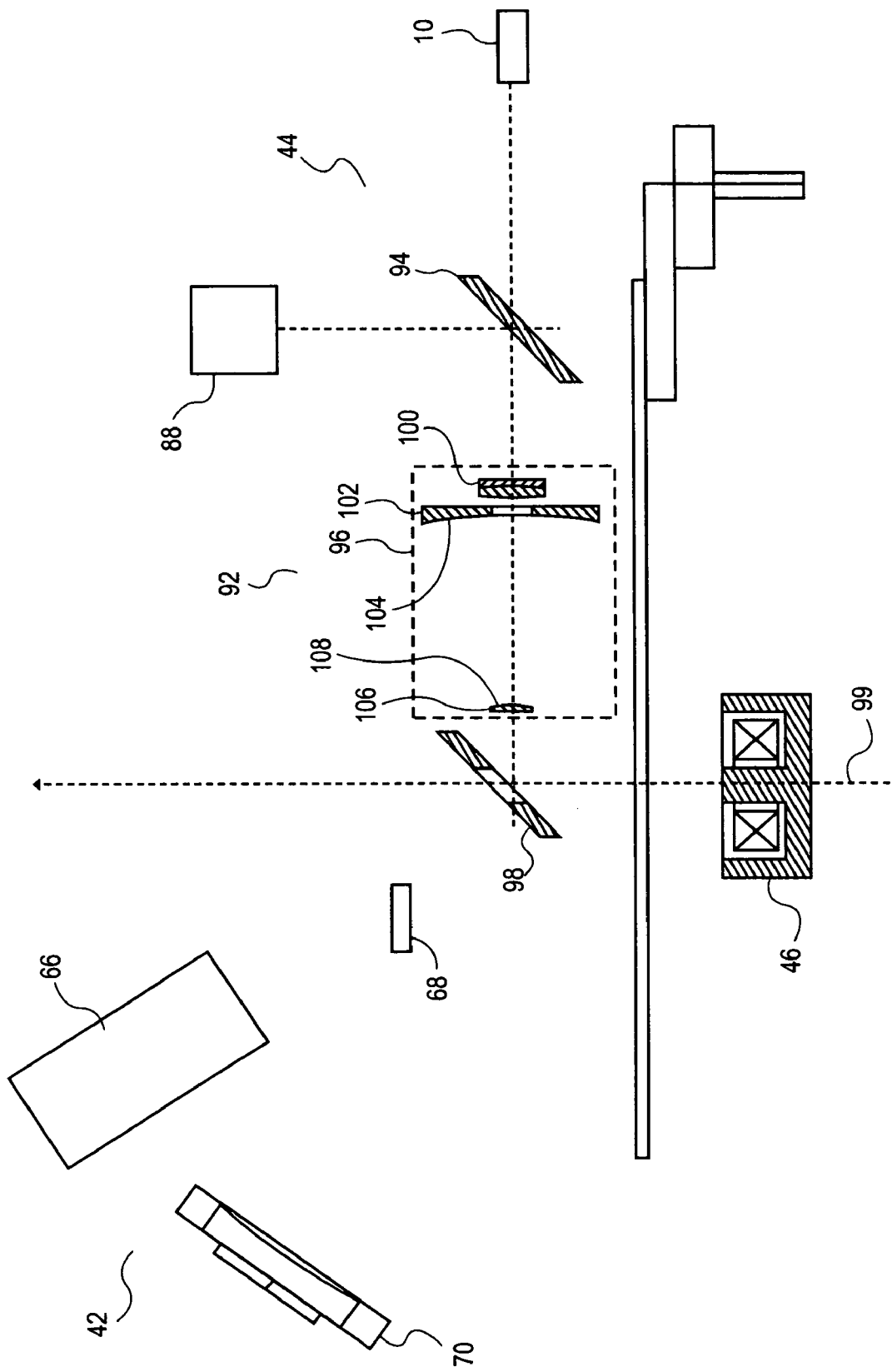

FIG. 1C illustrates the electromagnetic radiation source subsystem 42 and the viewing subsystem 44 in greater detail. The electromagnetic radiation source subsystem 42 may include an electron source 66, an anode 68, and a monochromator 70.

Figure 2:
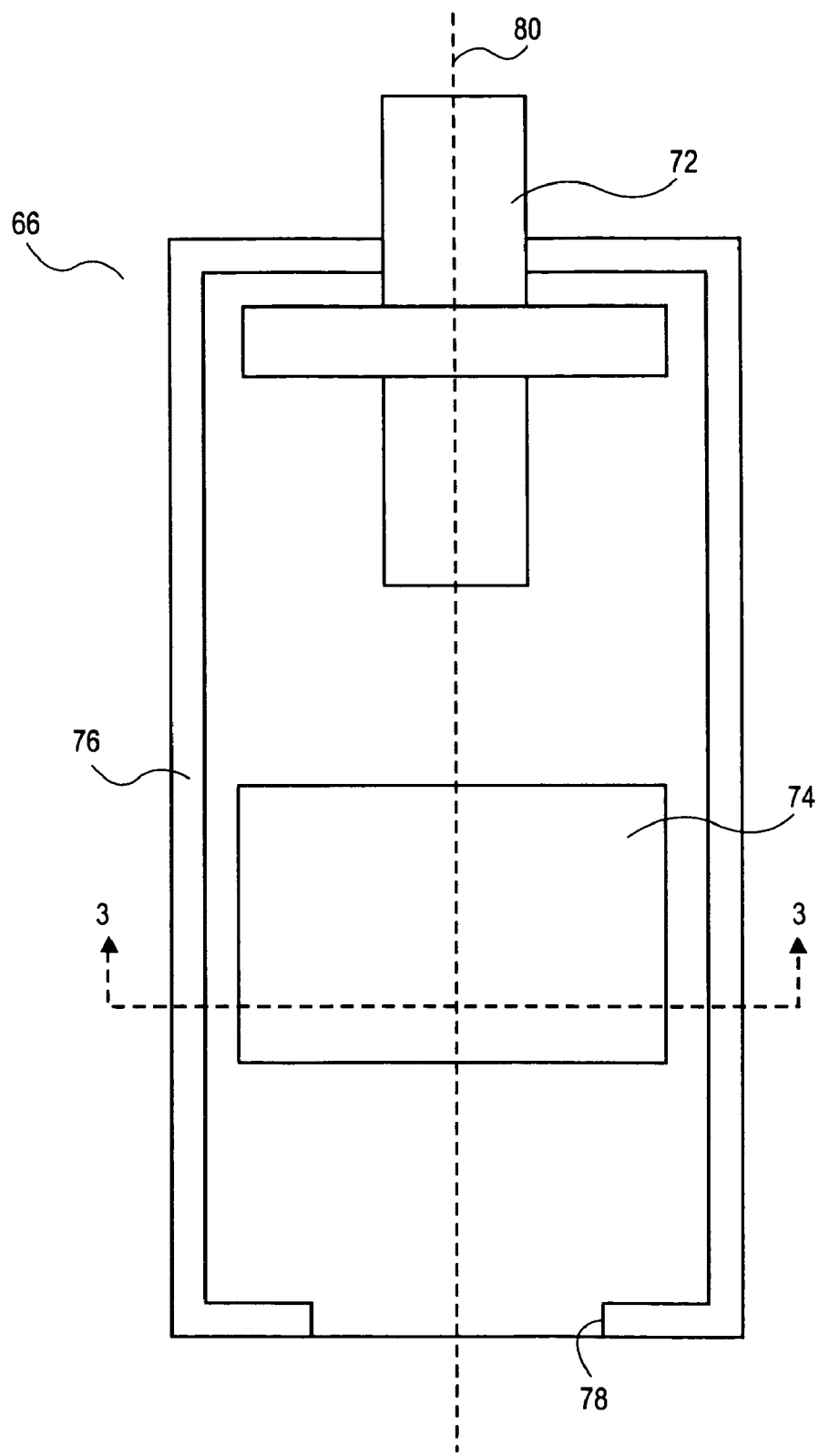
FIG. 2 is a cross-sectional side view of an electron source within the metrology chamber illustrated in FIG. 1.
Figure 3:
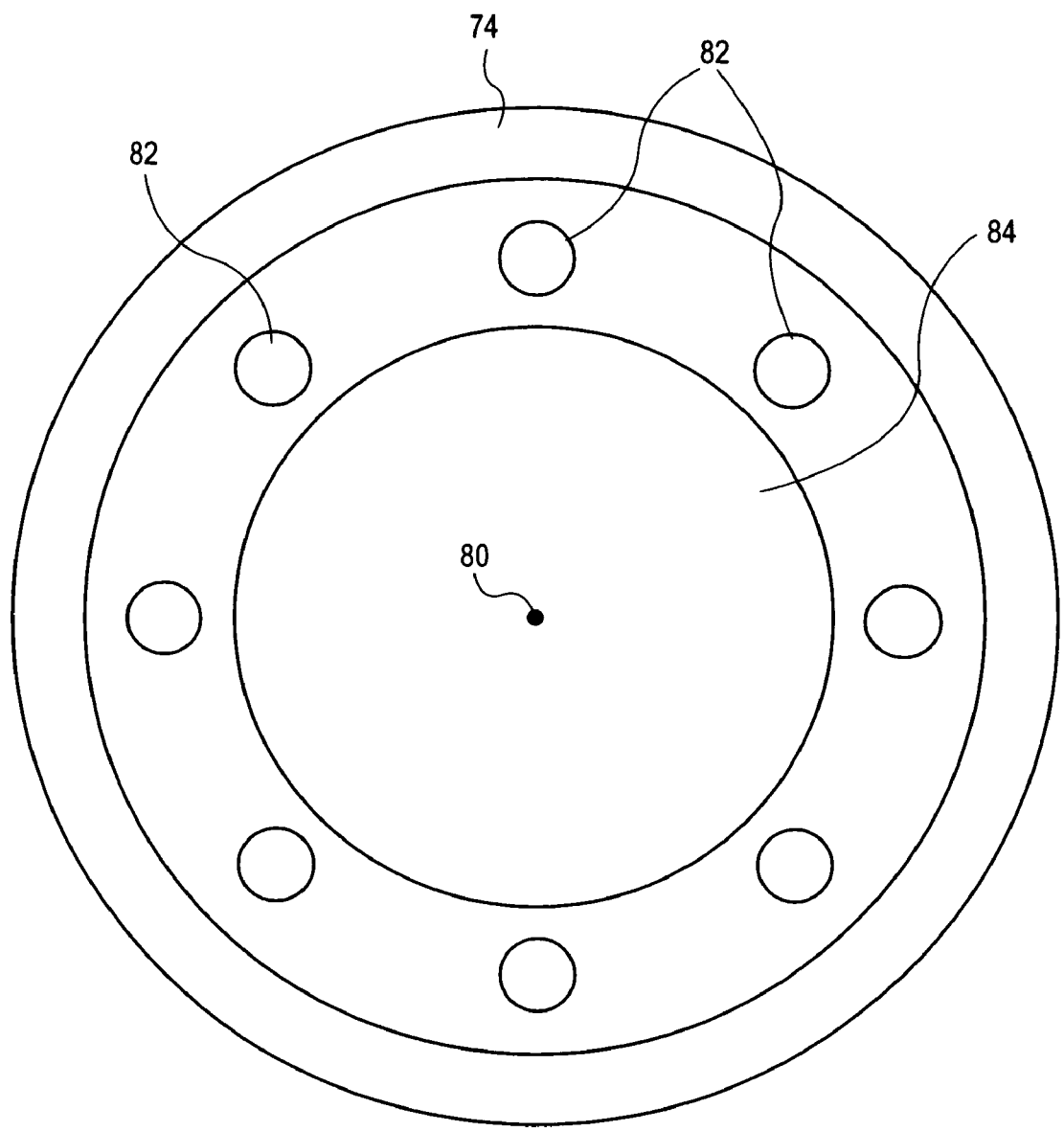
FIG. 3 is a cross-sectional view on 3-3 in FIG. 2 of a beam shaper within the electron source illustrated in FIG. 2.

Looking ahead to FIGS. 2 and 3, the electron source 66 may include an electron gun 72 and a beam shaper 74, both held within a casing 76. In cross section, the casing 76 may be substantially rectangular with the electron gun 72 mounted at a first end thereof. The casing 76 may have an opening 78 through an end thereof opposing the electron gun 72. As illustrated in FIG. 2, the electron gun 72 may have a central axis 80, which passes through the opening 78 in the casing 76.

FIG. 3 illustrates the beam shaper 74 in greater detail. In cross section, the beam shaper 74 may be substantially circular, include a plurality of poles 82, and have a beam shaper opening 84 extending therethrough. In the example illustrated in FIG. 3, the beam shaper 74 may have eight poles 82 positioned equally around the beam shaper opening 84. The central axis 80 of the electron gun 72, illustrated in FIG. 2, may extend through the beam shaper opening 84. As is commonly understood in the art, the poles 82 may form an "octopole" within the beam shaper 74, with each pole 82 being able to retain either a positive or negative electric charge. In an embodiment of the present invention, instead of using an "octopole" to shape the beam, an aperture or shutter can be used to mechanically change and control the shape of the electron beam.

Figure 4:
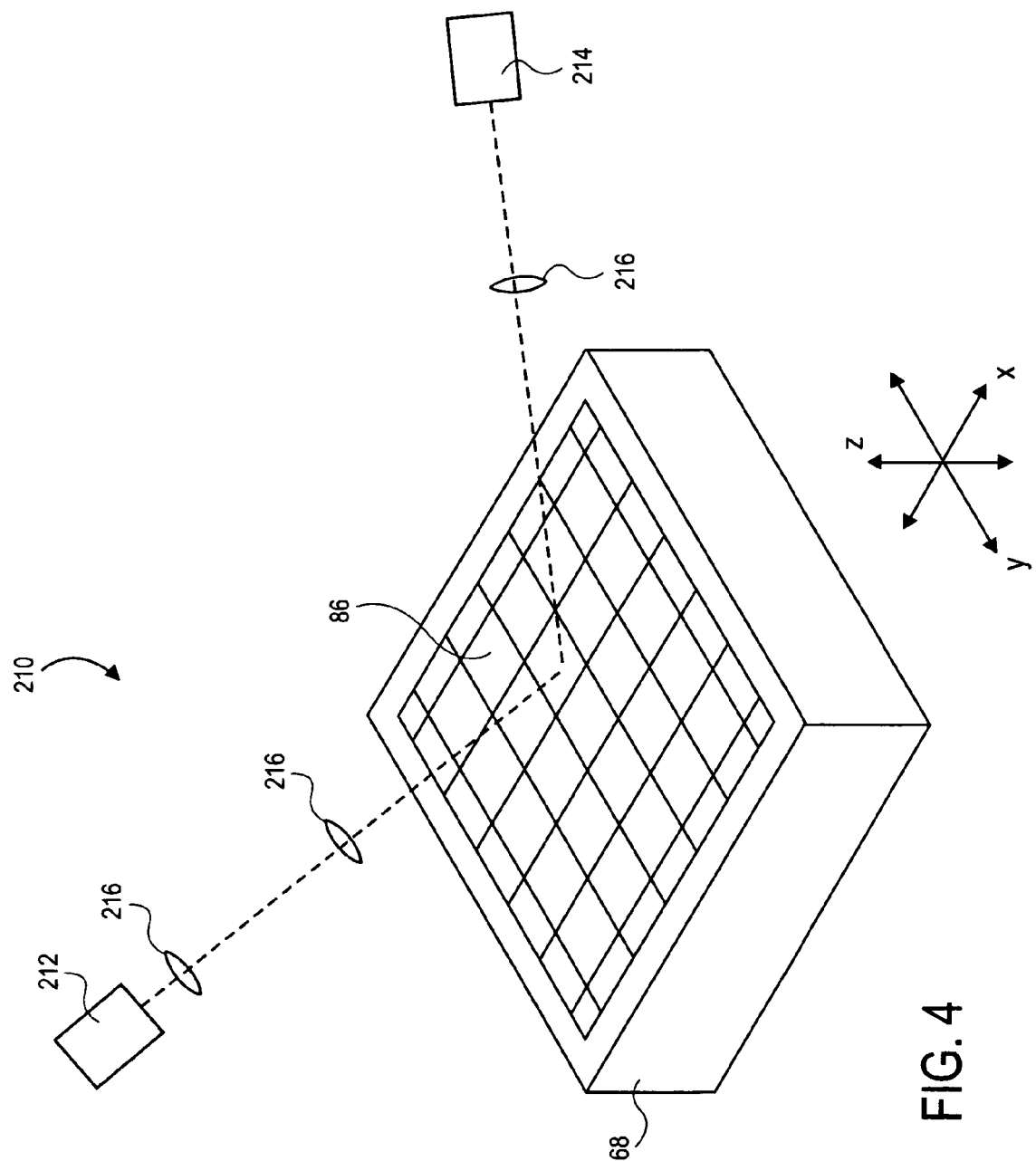
FIG. 4 is a perspective view of an anode within the metrology chamber illustrated in FIG. 1.

FIG. 4 illustrates the anode 68 in greater detail. The anode 68 may be substantially square with a target surface 86 on an upper side thereof and may be made of, for example, aluminum. Although not illustrated in detail, the anode 68 may be movably connected to chamber body 22 within the metrology chamber 30 to be capable of moving in an x/y/z coordinate system.

Referring again to FIG. 1C, the viewing subsystem 44 may include a camera 88, an illuminator 90, and a reflective subsystem 92. The reflective subsystem 92 may include a partial reflector 94, a focusing objective 96, and a deflection or turning mirror 98. The camera 88 may be positioned directly above the partial reflector 94 and directed, or aimed, at a central portion of the partial reflector 94. The illuminator 90 may be an optical light source positioned to the side of the partial reflector 94 and directed, or aimed, at the central portion of the partial reflector 94. The focusing objective 96 may be positioned to the side of the partial reflector 94 opposing the illuminator 90. The deflection mirror 98 may be positioned on a side of the focusing objective 96 opposing the partial reflector 94 and be positioned directly above the magnetic lens 46. The deflection mirror 98 may be substantially circular with an opening therethrough at a central portion thereof. As illustrated in FIG. 1C, a central axis 99 of the magnetic lens 46 may pass through the opening in the primary mirror 98. The central axis 99 may be defined as the axis upon which the magnetic field generated by the magnetic lens 46 has rotational symmetry.

Figure 5:
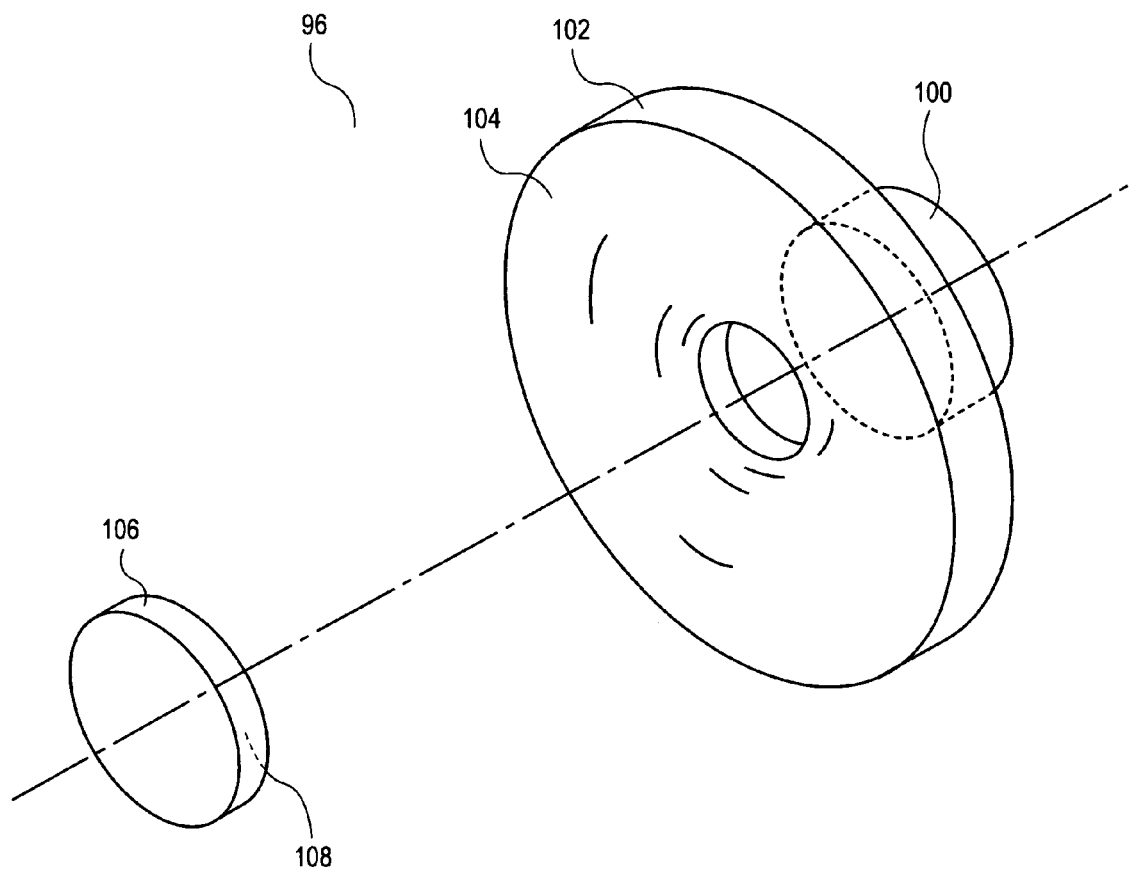
FIG. 5 is a perspective view of a focusing objective within the metrology chamber illustrated in FIG. 1.

Referring to FIG. 1C, in combination with FIG. 5, the focusing objective 96 may include a lens 100, a primary mirror 102, and a secondary mirror 106. Referring specifically to FIG. 5, the lens 100, the primary mirror 102, and the secondary mirror 106 may be substantially circular and centered about a common axis. Referring now to both FIGS. 1C and 5, the primary mirror 102 may have a concave reflective surface 104 and an opening at a central portion thereof. As illustrated specifically in FIG. 1C, the secondary mirror 106 may have a convex reflective surface 108.

It should be noted that the viewing subsystem 44, and all of the components thereof, may not have any moving, mechanical parts and be connected to the chamber wall 38 in a fixed position.

Figure 1D:
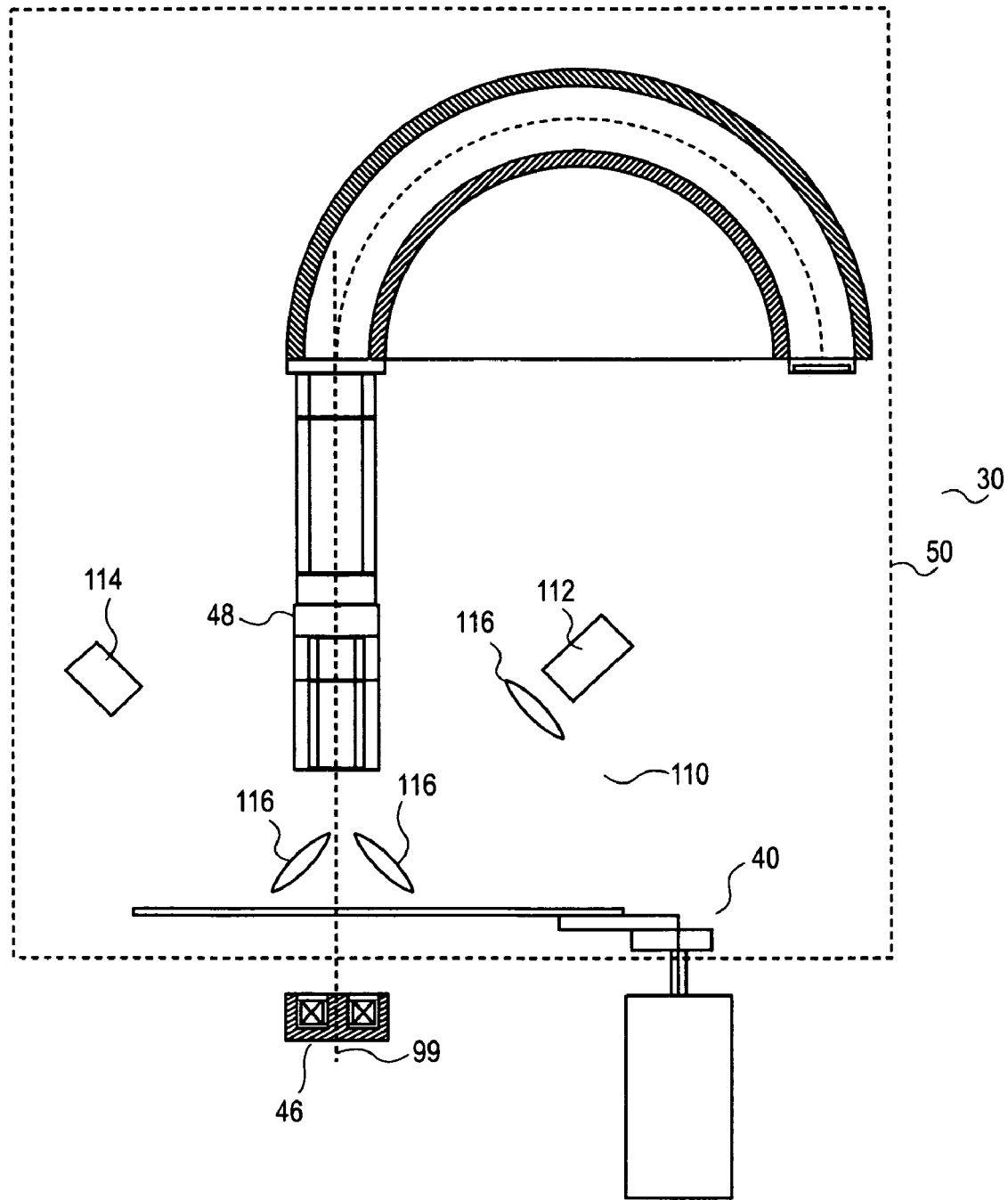

As illustrated in FIG. 1D, the metrology chamber 30 may also include a substrate height detection subsystem 110 including a laser 112, a laser detector 114, and an array of lenses 116 fixedly attached to chamber wall 38. The laser 112 and the laser detector 114 may be positioned on opposing sides of the metrological analyzer 48 and pointed toward the central axis 99 of the magnetic lens 46.

Similarly, as illustrated in FIG. 4, anode 68 may include an anode height detection subsystem 210 including a laser 212, a laser detector 214 and an array of lens 216 in order to determine and precisely control the height of anode 68. The laser 212 and laser detector 214 may be rigidly attached to chamber wall 38 and sighted at the focal point of monochromator 70 on anode 68.

Referring again to FIG. 1B, the metrological analyzer 48 may include an aperture positioned directly above the magnetic lens 46 and positioned such that the central axis 99 of the magnetic lens 46 passes therethrough. Although not illustrated in detail, the metrological analyzer 46 may also include a detector and an electron spectrometer or hemispherical analyzer, as is commonly understood in the art.

Although not illustrated in detail, it should be understood that all of the components of the metrology tool may be connected to the frame and include various actuators and power supplies to perform the various functions described below. In an embodiment of the present invention, electrical signal and power are delivered to and between various components in the vacuum chamber utilizing flex cables, such as polyimide flex circuits.

Referring again to FIG. 1A, the computer control console 32 may be in the form of a computer having a memory for storing a set of instructions and a processor connected to the memory for executing the instructions, as is commonly understood in the art. The instructions stored within the computer control console 32 may include methods and processes, as well as various algorithms to carry out the methods and processes, for the substrate movement and calibration, and operation of the metrology tool 20 as described below. The instructions may further include what is commonly understood to be "pattern recognition" software and software for translating between Cartesian and polar coordinates. Also, the instructions may include analytical software for using the components of the metrology tool 20 to determine the composition, including the concentrations, of various layers of a substrate, as well as determining the thicknesses of the various layers and the profile, depth distribution and depth distribution centroid of different chemical species within the layers.

The computer control console 32 may be electrically connected to the transport subsystem 26, the load-lock chamber 28, and the metrology chamber 30, as well as all of the components within the metrology chamber 30.

Figure 6:
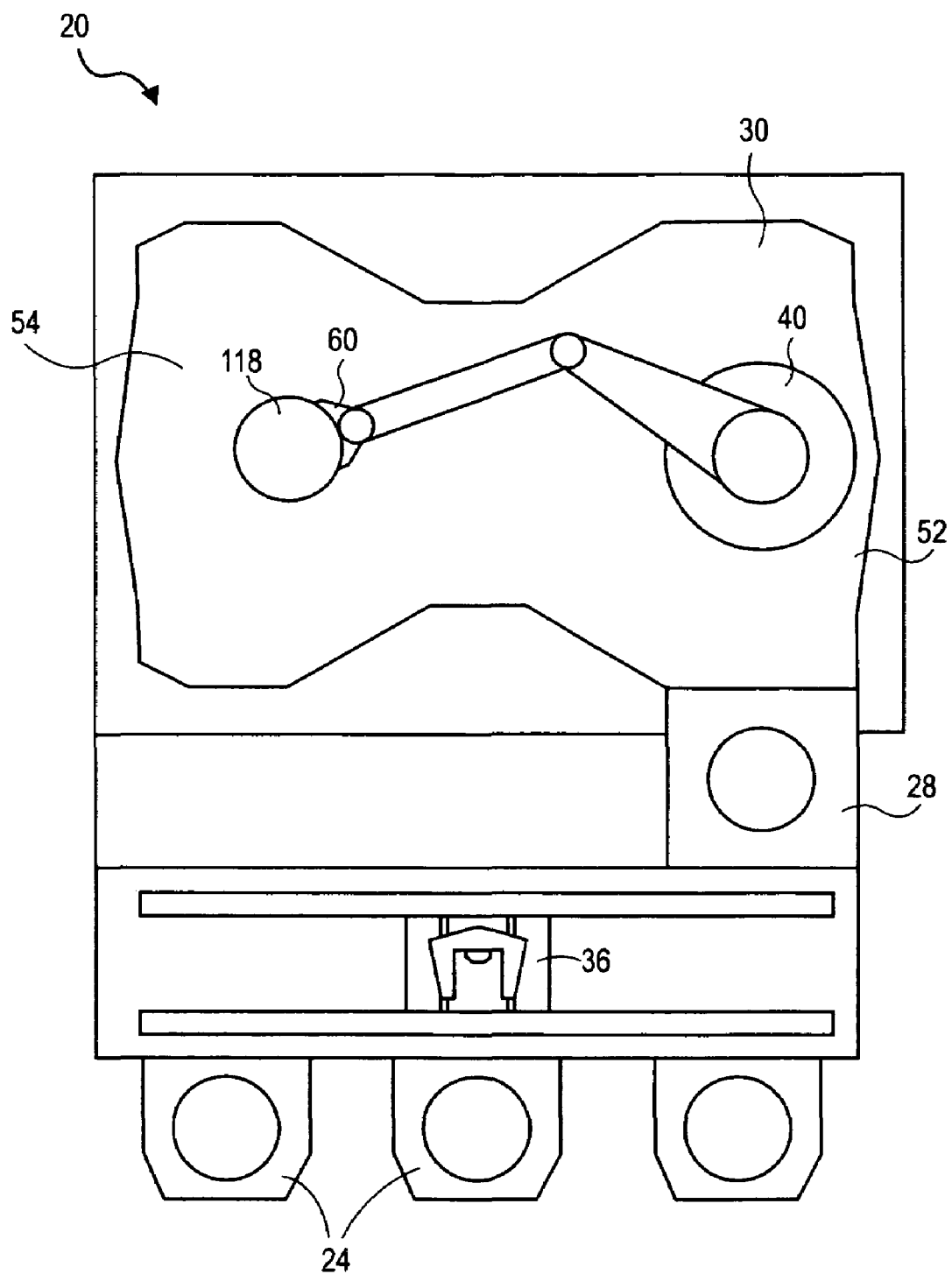
FIG. 6 is a top plan schematic view of the semiconductor substrate processing apparatus similar to FIG. 1.

In use, as illustrated in FIG. 6, a substrate 118 may be inserted into one of the substrate or wafer cassettes 24. A substrate for the purposes of the present invention is any sample, specimen, or article upon which photoelectron spectroscopy is to be carried out in apparatus 20. A substrate may include, but not limited to, a semiconductor wafer, such as silicon monocrystalline substrate, a silicon-on-insulator substrate, or other types of substrates used in the manufacture of integrated circuits, photomasks, flat panel displays, or optical components. Additionally, a substrate may include one or more-thin films or layers, such as metal layers, semiconductor layers, and dielectric layers used to fabricate features, such as but not limited to gate dielectric layers, gate electrodes, barrier layers, interconnects, contacts, passivation layers, and micro-machines. In a specific embodiment of the present invention, the substrate is a monocrystalline silicon wafer having a gate dielectric layer, such as a silicon oxynitride dielectric or a metal oxide dielectric, such as hafnium oxide or aluminum oxide, formed thereon. In an embodiment of the present invention, apparatus 20 is used to determine the thickness, composition, and dopant profile of a gate dielectric layer. The transport mechanism 36, may retrieve the substrate 118 from the cassettes 24 and transport the substrate 118 into the load-lock chamber 28. The robotic stage 40 may then retrieve the substrate 118 from the load-lock chamber and carry the substrate 118 from the first portion, or loading portion, 52 of the metrology chamber 30 to the second portion, or testing portion, 54 of the metrology chamber 30.

Figure 7:
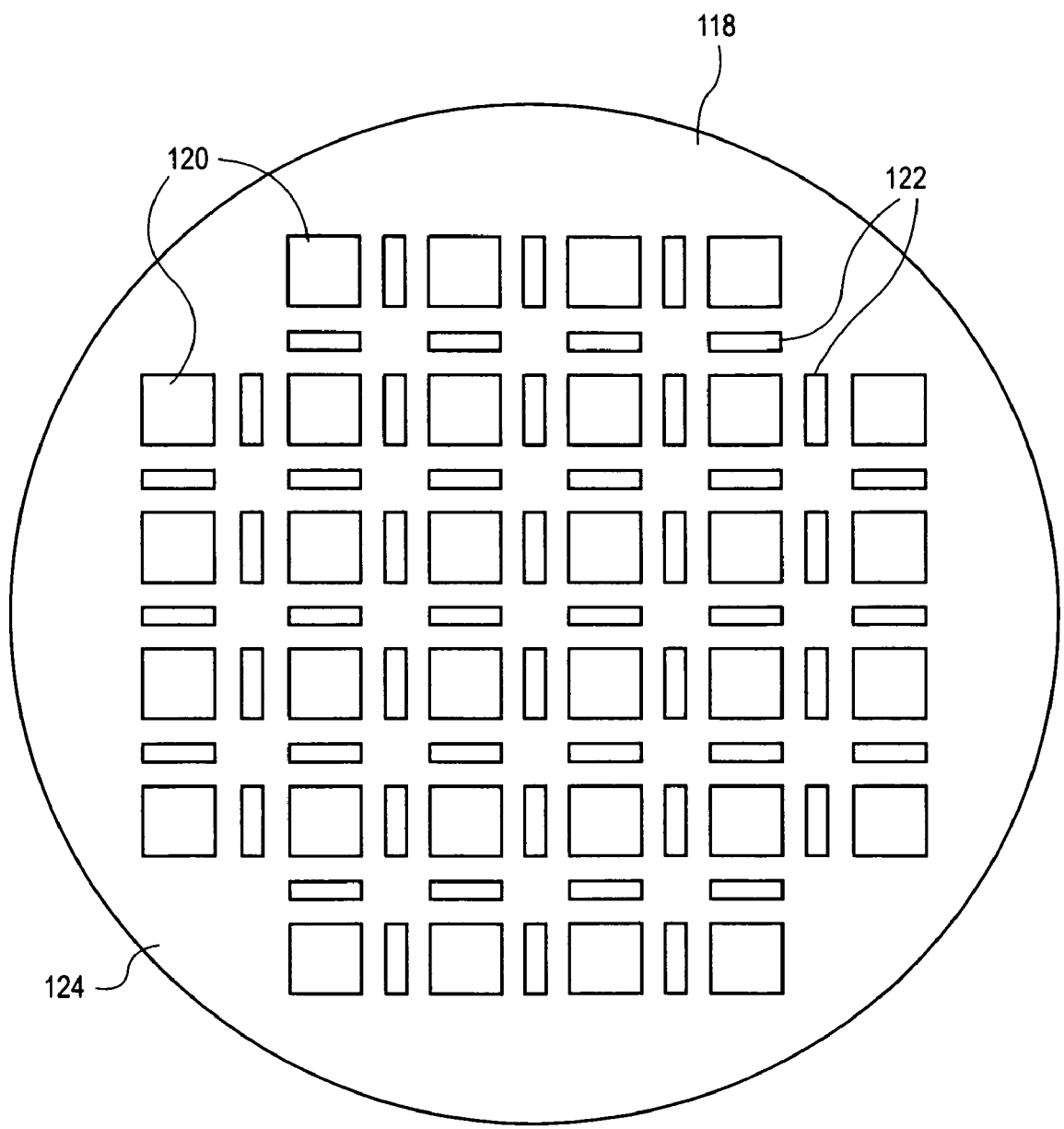
FIG. 7 is a top plan view of a semiconductor substrate.

FIG. 7 illustrates the substrate 118 in greater detail. The substrate 118 may be a semiconductor wafer, as is commonly understood in the art, with a diameter of, for example, 200 or 300 millimeters. The substrate 118 may have a plurality of integrated circuits 120 formed thereon and divided amongst multiple dice. The formation of the integrated circuits 120 may only be partially completed. The substrate 118 may also include a plurality of metrology pads 122, as is commonly understood in the art, located between the integrated circuits 120. The metrology pads 122 may be, for example, substantially rectangular with dimensions of 120 microns by 50 microns. Rectangular metrology pads with one side larger than the other are ideal because they enable a large area pad to be placed in the "scribe lines" between the product dice. The large area pads enable increase number of electrons to be extracted from the metrology pad during testing and thereby provide more information about the substrate surface. The integrated circuits 120 and the metrology pads 122 may be formed on an upper surface 124 of the substrate 118.

Figure 8A:
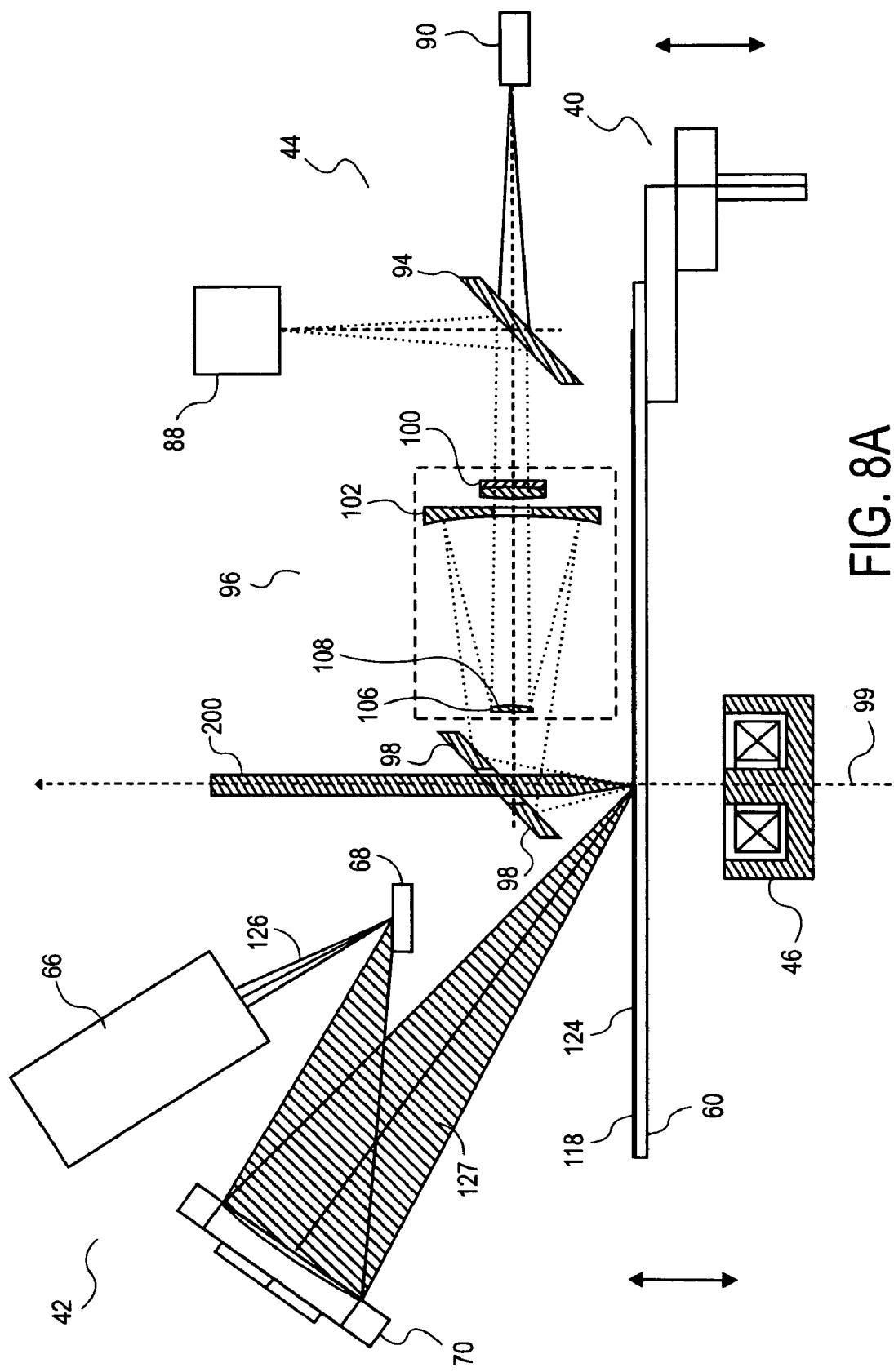
FIG. 8A is a cross-sectional side schematic view of the metrology chamber similar to FIG. 1C.

As illustrated in FIG. 6 in combination with FIG. 8A, the robotic stage may position the substrate 118 between the magnetic lens 46 and the deflection mirror 98 such that the magnetic lens 46 and the metrological analyzer 48 are on opposing sides of the substrate support 60. The computer control console 32 may control the robotic stage 40 in such a way that when the robotic arm 58 is moved, the substrate support 60, the first segment 62 of the robotic arm 58, and the second segment 64 of the robotic arm 58 do not contact the chamber wall 38. As illustrated specifically in FIG. 8A, the robotic stage 40 may position the substrate 118 between the deflection mirror 98 and the magnetic lens 46.

It should be noted that, when the substrate support 60 is holding the substrate 118 within the second portion 54 of the metrology chamber 30, because the base 56 of the robotic stage 40 is located within the first portion 52 of the metrology chamber 30 and does not interfere with the positioning of the magnetic lens 46, the distance between the substrate support 60 and the magnetic lens 46 may be particularly small. The distance between an upper surface of the magnetic lens 46 and the lower surface of the substrate support 60 may be less than 5 millimeters, such as between 2 and 4 millimeters. Additionally, the distance from the upper surface 124 of the substrate 118 and the magnetic lens 46 may be less than 8 millimeters.

Still referring to FIG. 8A, the robotic stage 40 may position the substrate 118 such that a particular one of the metrology pads 122, illustrated in FIG. 7, is intersected by the central axis 99 of the magnetic lens 46 (i.e., a first testing position). In order to verify that the substrate 118 is properly positioned, the computer control console, illustrated in FIG. 1A, may utilize the viewing subsystem 44 as illustrated in FIG. 8A.

Referring to FIGS. 5 and 8A, optical light may be directed by the illuminator 90 through the partial reflector 94 and into the focusing objective 96. The light may pass through the lens 100 and the opening within the primary mirror 102. The light may then be reflected off the reflective surface 108 of the secondary mirror 106 back toward the primary mirror 102. The concave reflective surface 104 of the primary mirror may reflect the light around the outer edges of the secondary mirror toward the deflection mirror 98 as illustrated in FIG. 8A.

The light may then be reflected by the deflection mirror 98 onto the portion of the substrate (i.e., the particular metrology pad 122 in the first testing position), which is intersected by the central axis 99 of the magnetic lens 46. The light being reflected off of the deflection mirror 98 onto the substrate 118 may be considered to be in a bundle with a central axis that is coaxial to the central axis 99 of the magnetic lens 46. The light may then be reflected off the substrate 118 back through the reflective system 92 and into the camera 88. Using the pattern recognition software described above, the computer control console 32, as illustrated in FIG. 1A, may be able to determine whether or not a metrology pad 122 as illustrated in FIG. 7 is located properly in the testing position.

The viewing subsystem 44 is able to view the portion of the substrate 118 being tested at an angle normal, or directly downward, on the substrate 118 while the testing is taking place.

Still referring to FIG. 8A, the electromagnetic radiation source subsystem 42 may then be activated to direct x-rays onto the substrate 118. Referring now to FIG. 2, the electron gun 72 within the electron source 66 may be activated to emit a beam of electrons 126 through the beam shaper 74 and out of a casing 76 through the opening 78.

Figure 8B:
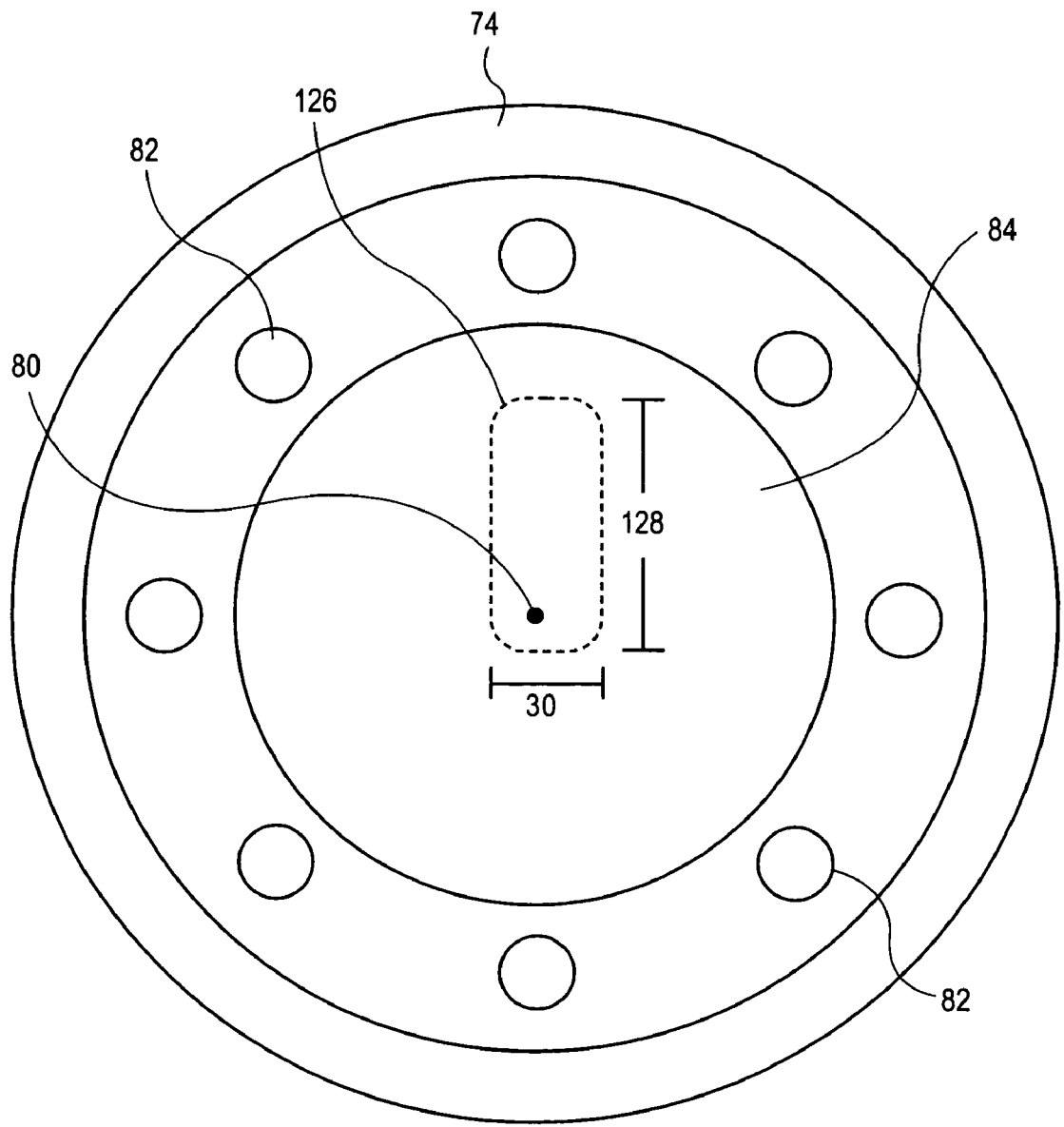
FIG. 8B is a cross-sectional view of the beam shaper similar to FIG. 3.

FIG. 8B illustrates the beam shaper 74 as the beam of electrons 126 passes therethrough. Various positive and negative electrical charges may be supplied to the poles 82 within the beam shaper so that a particular electric field is generated within the beam shaper opening 84. As illustrated specifically in FIG. 8B, as the beam of electrons 126 passes through the beam shaper opening 84, the beam 126 may be shaped, or defocused, in a particular direction. In the example illustrated, the beam 126 is shaped to have a substantially rectangular cross-section, or shape, with a length 128 and width 130. The length 128 may extend substantially in a first length direction 132 and the width 130 may extend substantially in a first width direction 134. Referring once again to FIG. 8A, the beam may leave the electron source 66 and be directed onto the anode 68.

Figure 8C:
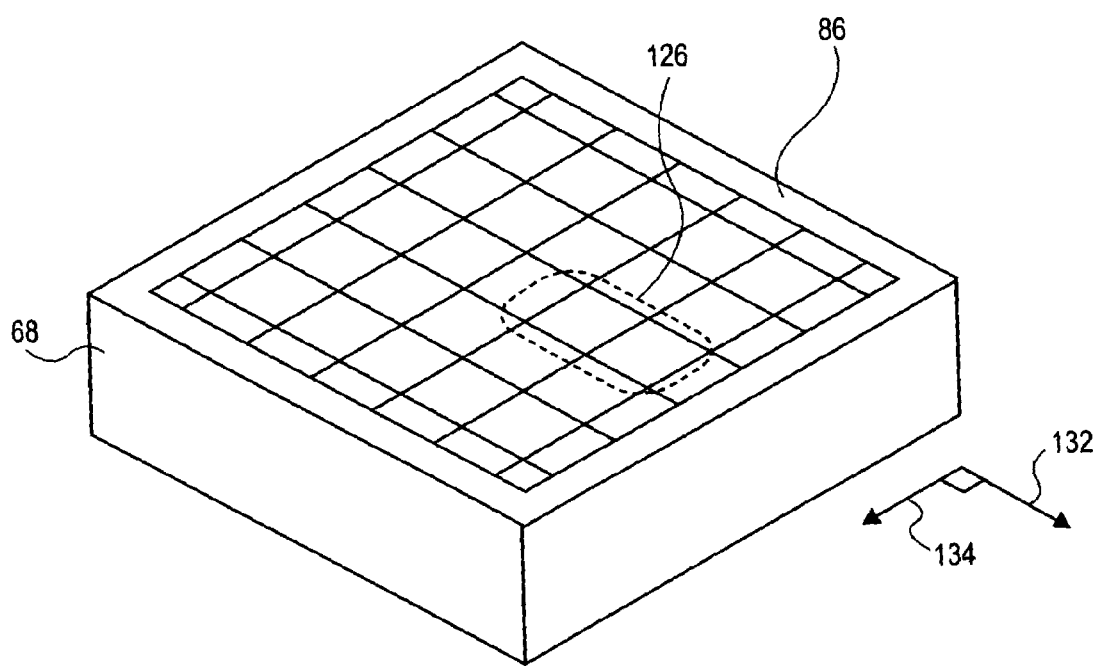
FIG. 8C is a perspective view of the anode similar to FIG. 4.

FIG. 8C illustrates the anode 68 as the beam of electrons 126, illustrated in FIG. 8B, strikes the anode target surface 86. As shown, the beam 126 may still have a substantially rectangular shape with the length 128 extending in the first length direction 132 and the width extending 130 in the first width direction 134. At the target surface of the anode, although not illustrated in detail, for example, the length 128 of the beam 126 may be approximately 84 microns and the width of the beam 126 may be approximately 45 microns. The power of the beam 126 may be, for example, more than 100 watts such as approximately 200 watts. In an embodiment of the present invention, the e-beam is shaped to produce an elongated e-beam profile having an aspect ratio (length:width) greater than 1:1 and preferably greater than 2:1 and in some embodiments greater than 3:1. In an embodiment of the present invention, an e-beam profile having length between 20 and 200 microns and a width between 20 and 200 microns is formed. Additionally, in an embodiment of the present invention, the power of the e-beam is between 4 and 200 watts. As is commonly understood in the art, the electrons striking the anode 68 may cause x- rays to be emitted from the material of the anode 68. It is to be appreciated that an anode can only withstand a certain e-beam power level per area without being damaged. By forming an elongated beam and by increasing the area of the beam, more power can then be placed in the beam, thereby enabling more X-rays to be generated without damaging the anode. Doubling the area of the e-beam enables doubling of the power applied to the anode without damaging the anode.

Referring back again to FIG. 8A, the beam of x-rays 127 may propagate from the anode 68 onto the monochromator 70, which redirects and focuses only selected frequencies of the x-rays toward the substrate 118.

Figure 8D:
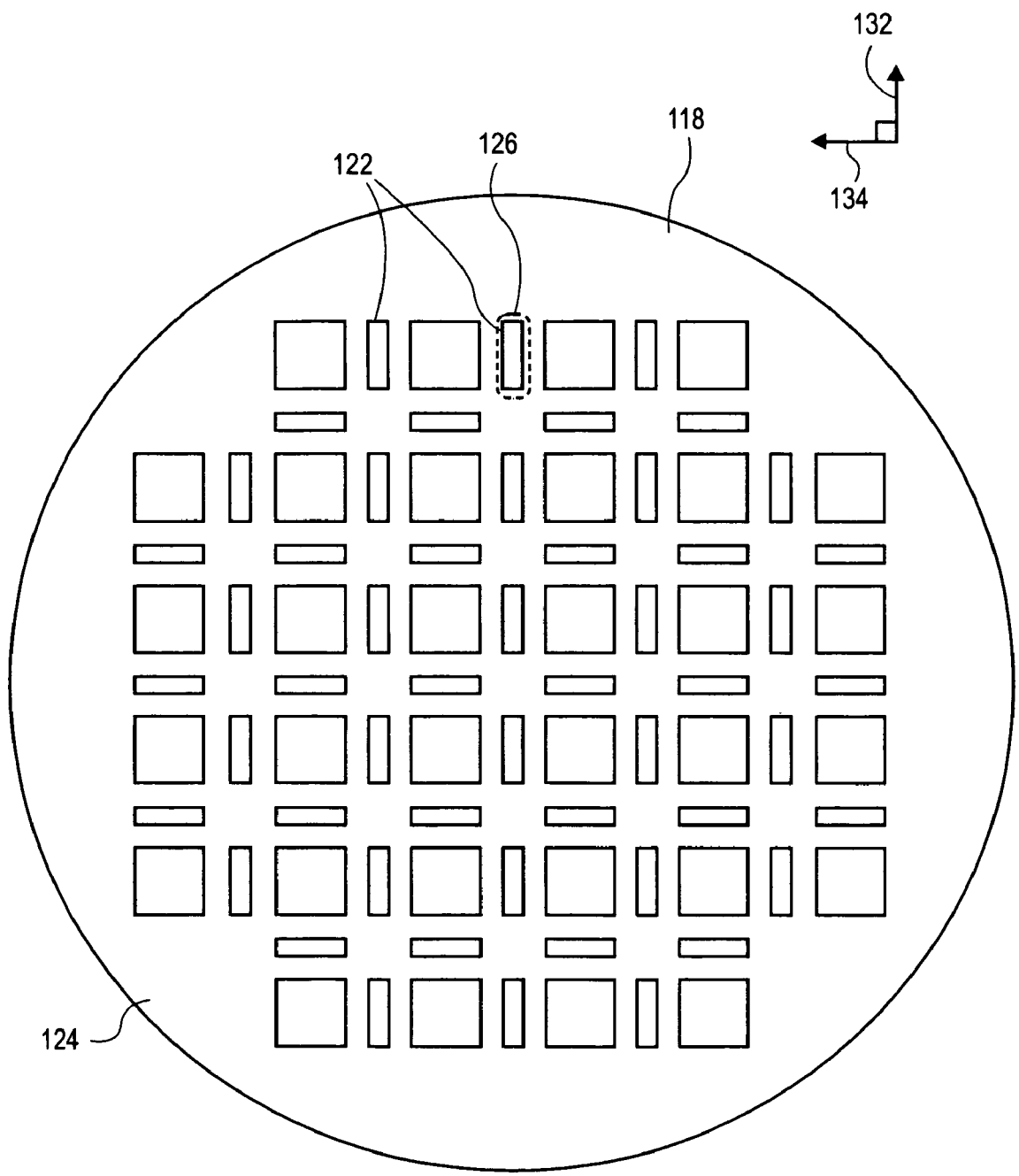
FIG. 8D is a top plan view of the semiconductor substrate similar to FIG. 7.

FIG. 8D illustrates the substrate 118 as the beam of x-rays 127 strikes the upper surface 124 thereof. As shown, the X-ray beam 127 may maintain the same relative shape and orientation on the substrate 118 as the shape, size and orientation of the e-beam on anode 68. The x-ray beam 127, however, may take on a slightly larger size than ebeam 126. The use of a large area monochromator with a large collection angle enables the shape of the X-ray beam 127 on substrate 118 to be highly correlated with the shape and orientation of the e-beam 126 on anode 68. In an embodiment of the present invention, the X-ray beam has an elongated oval or rectangular shape with an aspect ratio (length:width) of at least 1:1, and preferably greater than 2:1, and in some embodiments greater than 3:1. In a specific embodiment X-ray 127 may have a length of more than 100 microns, specifically in the example illustrated, approximately 110 microns and a width of approximately 40 microns to match the dimensions of the metrology pad 122.

For illustrative purposes, despite the fact that the e-beam 126 and X-ray beam 127 have been directed off of several surfaces, the image formed by the beam may still be considered to have a length extending in the first length direction 132 and a width extending in the first width direction 134.

As is commonly understood in the art, referring to FIG. 8A in combination with FIG. 1B, as the x-rays 127 bombard the material on the substrate 118, at the atomic level, electrons within the material on the metrology pad 122 may become energized and be ejected from their respective orbitals of the atoms within the materials on the metrology pads of the substrate 118.

As will be appreciated by one skilled in the art, the magnetic lens 46 may be activated to generate a magnetic field within the metrology chamber 30, which has a rotational symmetry about the central axis 99 of the magnetic lens 46. Thus, the electrons, or photoelectrons 200, may be guided by the magnetic field directly upwards along the central axis 99, pass through the opening within the deflection mirror 98, and enter the aperture and the detector of the electron spectrometer or hemispherical analyzer of the metrological analyzer 48. As the photoelectrons propagate from the substrate 118 to the analyzer 48, the photoelectrons may be arranged in a bundle with a central axis which is coaxial with the central axis of the bundle of visible light and the central axis 99 of the magnetic lens 46. Thus, the direction in which the visible light from the viewing subsystem 44 propagates onto the substrate 118 may be substantially parallel to the direction in which the photoelectrons propagate from the substrate 118 into the analyzer 48.

It should be noted that because of the close proximity of the magnetic lens 46 to the substrate 118, the effectiveness of the magnetic field in guiding the photoelectrons is maximized. Additionally, as illustrated in FIG. 1B, because the magnetic lens is not positioned within the vacuum chamber 50, if the magnetic lens requires any maintenance, the magnetic lens 46 may be accessed without exposing the components within the vacuum chamber to outside air.

The electron spectrometer or hemispherical analyzer may determine the composition of a material on the metrology pad on a substrate 118 based on the kinetic energy, or speed, of the electrons.

Additionally, as previously mentioned, the metrology tool 20 may also determine the thicknesses of the various layers and the profile, distribution and depth distribution centroid of different chemical species within the layers upon substrate 118.

Figure 9A:
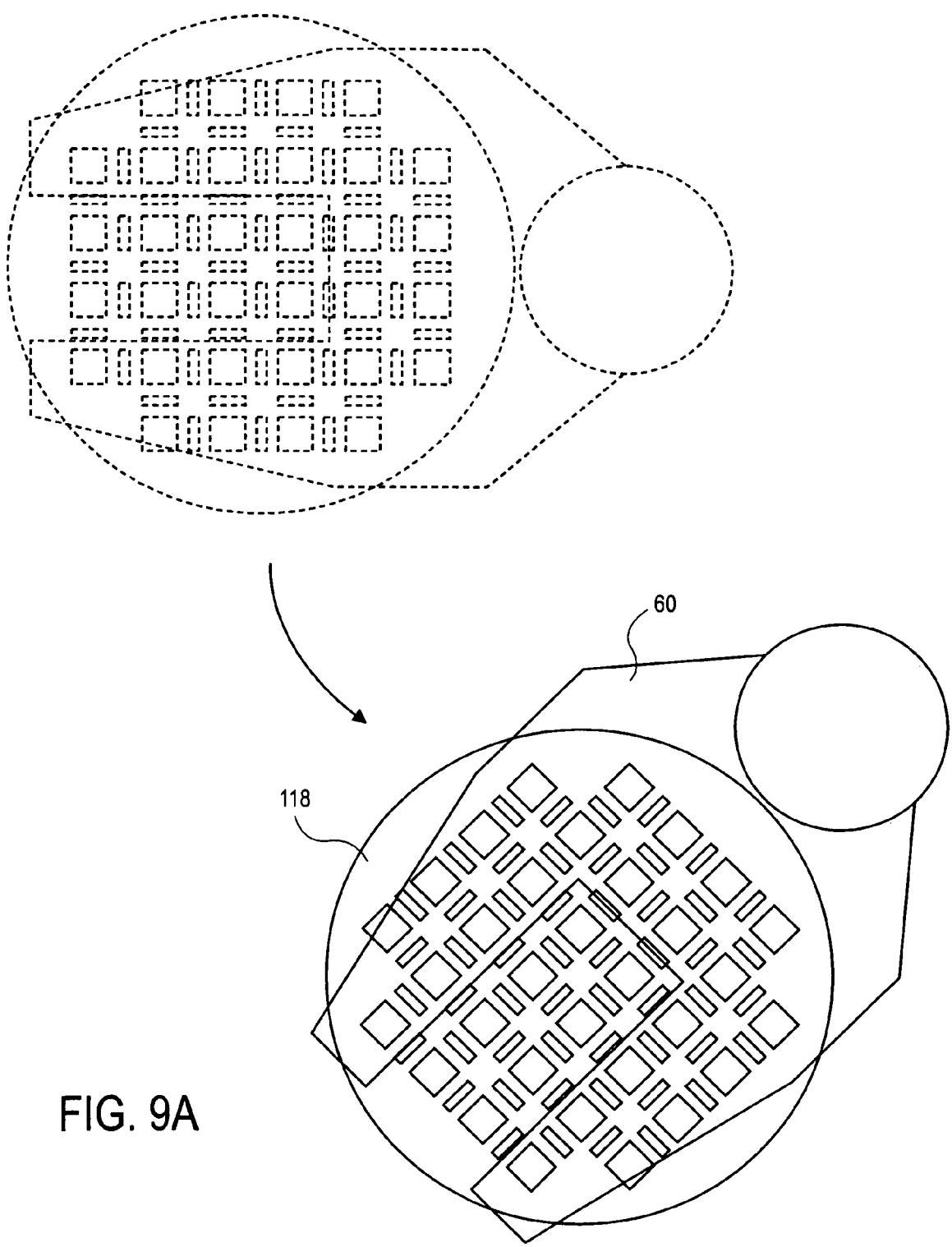
FIG. 9A is a top plan view of a semiconductor substrate within the metrology chamber illustrated in FIG. 1 showing movement thereof.

As illustrated in FIGS. 8A and 9A, the substrate support 60 may then be moved to position a different metrology pad 122 above the central axis 99 of the magnetic lens 46 (i.e., a second testing position). As described above, because of the structure of the robotic stage 40, the substrate support 60 may move the substrate 118 in a polar coordinate system (R, θ). Thus, when the substrate 118 is moved to test a different metrology pad 122, the substrate 118 may undergo a rotation such that the metrology pads 122 are oriented differently with respect to the remainder of the metrology chamber 30 when compared to the first testing position.

Referring again to FIG. 8A, the electron source 66 may again be activated to direct electrons onto the anode 68.

Figure 9B:
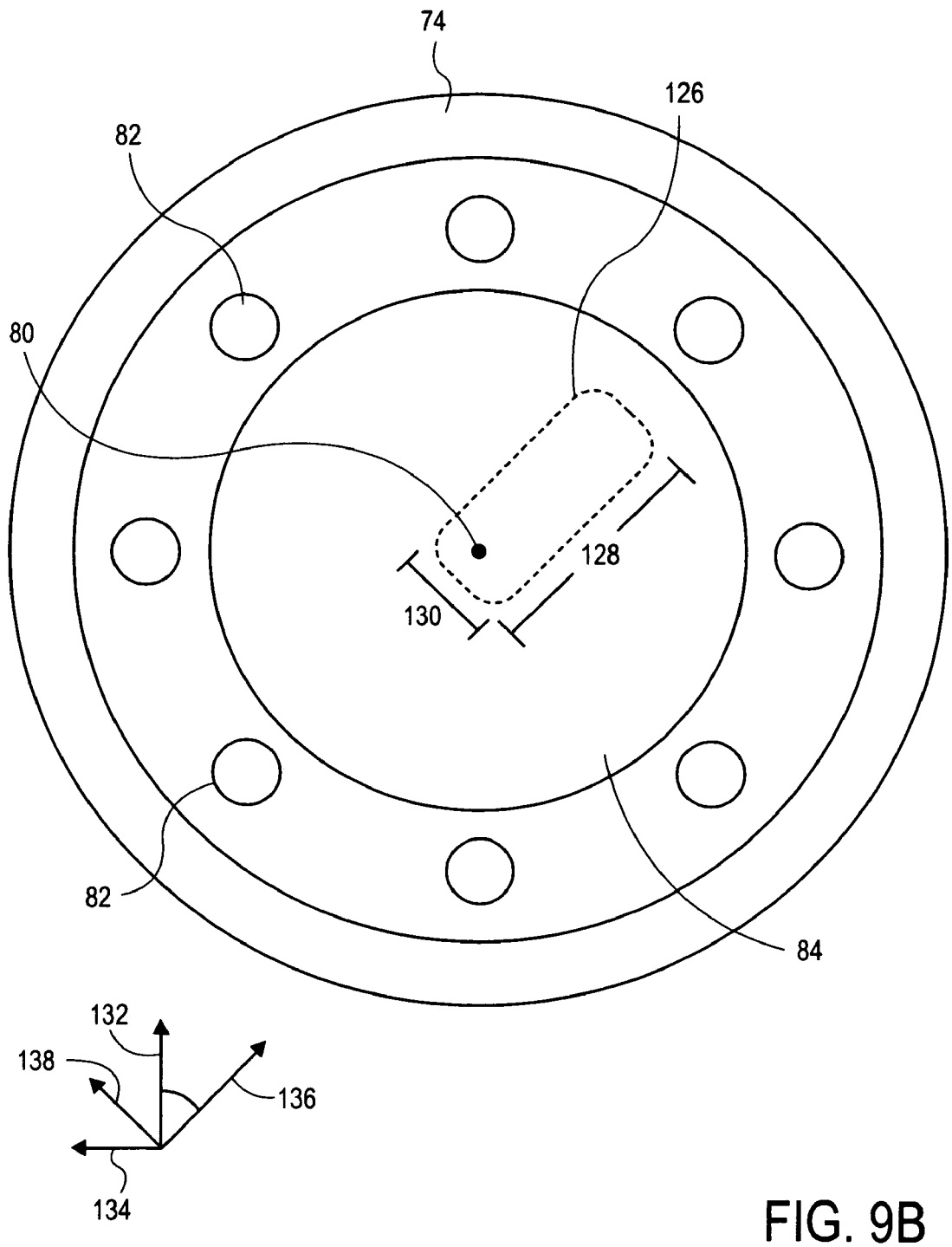
FIG. 9B is a cross-sectional view of the beam shaper similar to FIGS. 3 and 8B.

FIG. 9B illustrates the beam shaper 74 within the electron source 66 as the substrate 118 is oriented as shown in FIG. 9A. As shown in FIG. 9B, in order to match the rotated orientation of the substrate, a different electric field may be generated by the poles 82. As shown, the beam 126 may still be substantially rectangular in shape, however, the length 128 and the width 130 of the beam 126 may be rotated relative to the beam 126 illustrated in FIG. 8B. As shown in FIG. 9B, the length 128 may now extend in a second length direction 136 and the width 130 may now extend in a second width direction 138.

Figure 9C:
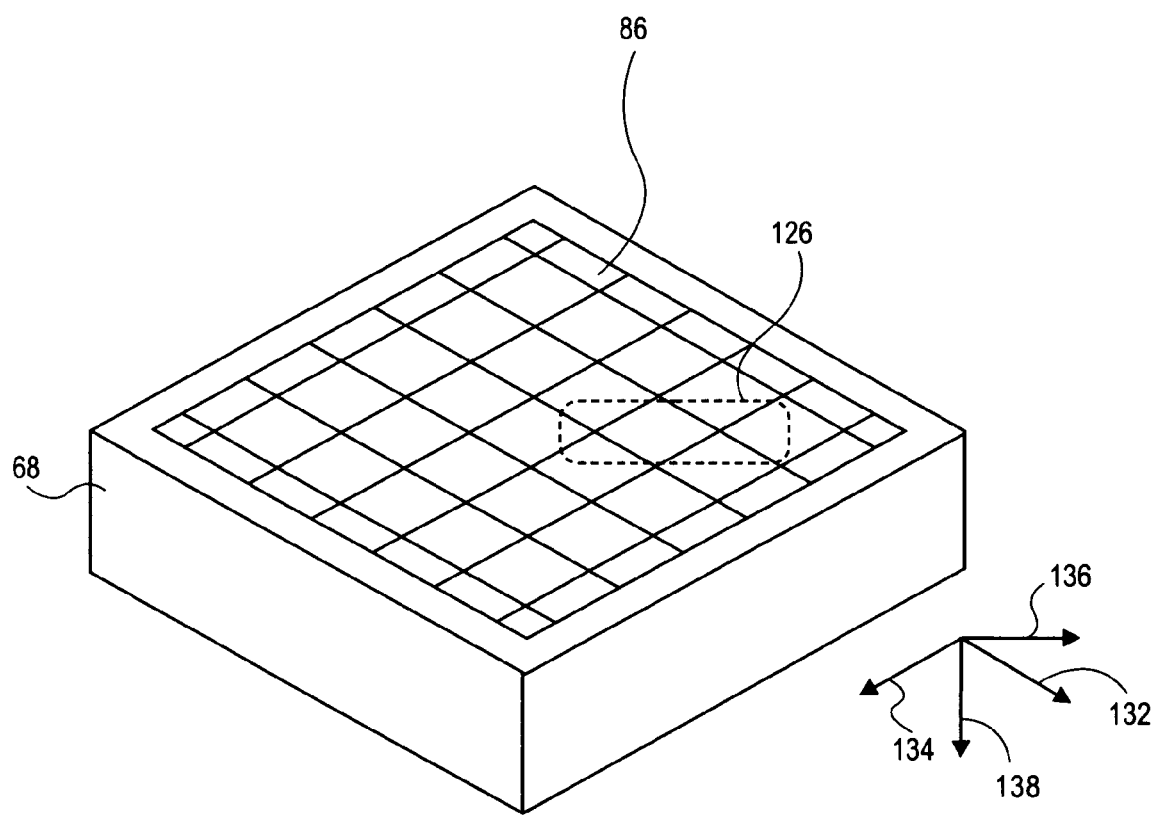
FIG. 9C is a perspective view of the anode similar to FIGS. 4 and 8C.

FIG. 9C illustrates the anode 68 as the beam 126 illustrated in FIG. 9B strikes the anode target surface 86. As shown, the beam 126, as indicated on the anode target surface 86, may have been rotated relative to the beam 126 on the anode target surface 86 illustrated in FIG. 8C.

Additionally, in order to expose "fresh" material on the anode 68, the anode 68 may have been moved in the x/y plane so that a second portion of the target surface 86 of the anode 68 may be struck with the beam 126. Therefore, the number of x-rays, which propagate from the anode 68 may be maximized. The second portion of the anode that is struck with the beam may at least partially overlap the portion that the beam 126 initially struck.

Figure 9D:
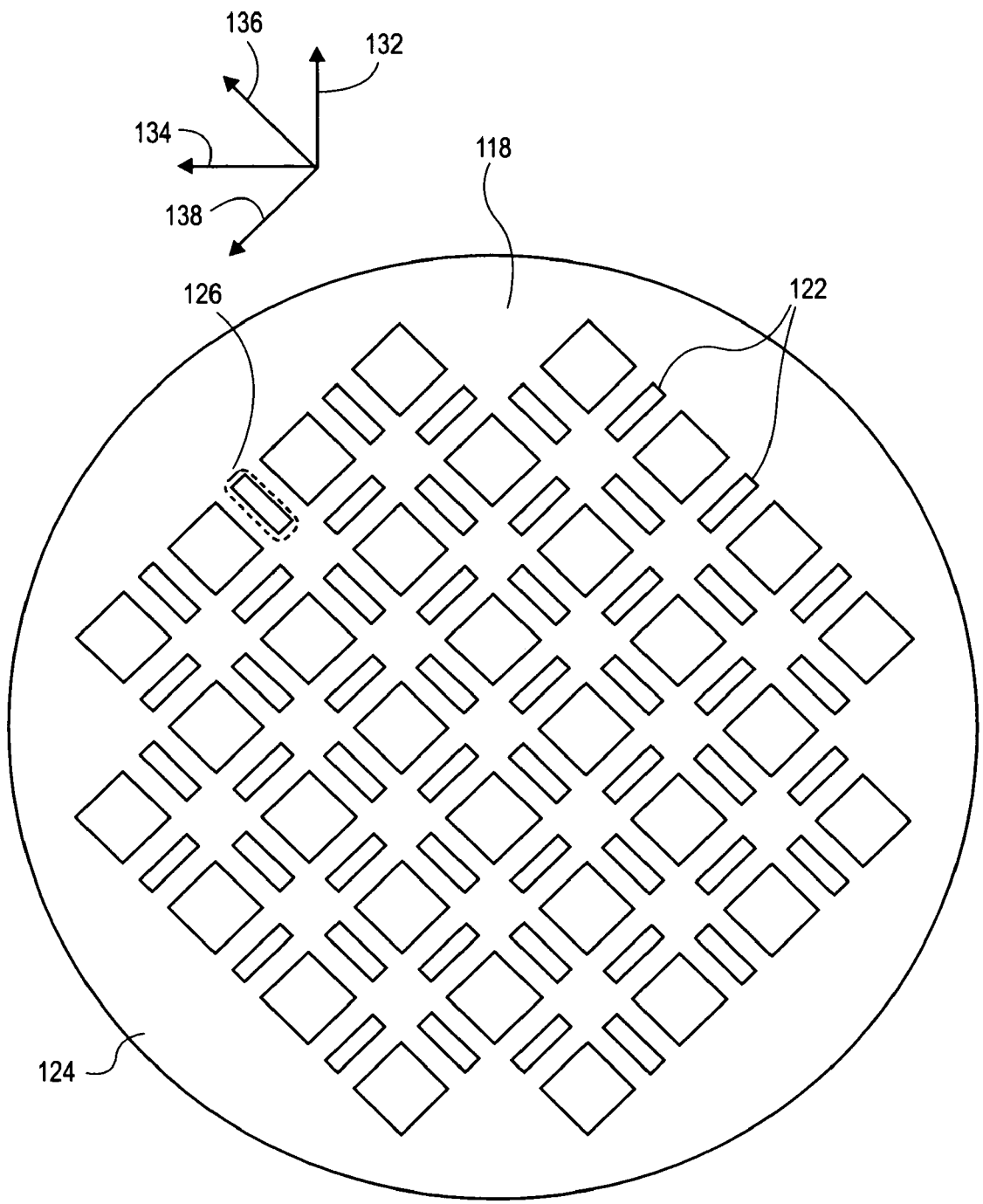
FIG. 9D is a top plan view of the semiconductor substrate similar to FIGS. 7 and 8D.

As described above, and illustrated in FIG. 8A, x-ray 127 may be propagated from the anode 68 and redirected by the monochromator 70 onto the substrate 118. FIG. 9D illustrates the substrate 118 in the angular orientation shown in FIG. 9A, as the beam 127 strikes the upper surface 124 thereof. As shown, the beam 127 has been rotated to match the angular orientation of the metrology pads 122. Therefore, the beam 127 is capable of substantially covering the entire metrology pads 122 despite the fact that the metrology pads 122 have been rotated.

Referring again to FIG. 8A in combination with FIG. 1B, electrons may be emitted by the materials on the metrology pad 122 through the opening in the primary mirror 98 and into the metrological analyzer 48 as described above.

The rotating, or shaping, the nature of the electron beam described above, increases the speed at which substrates may be tested, particularly when the robotic stage moves the substrates in a polar coordinate system. The efficiency and accuracy of the testing is also improved by moving the beam of electrons on the target surface of the anode, as the number of x-rays which strike the substrate, as well as the number of photoelectrons which are collected by the metrological analyzer, is maximized.

Additionally, it is to be appreciated that the combination of beam shaping and the viewing system enables a fast and accurate acquisition of metrology targets across the surface of substrate 118 when utilizing robot 40 as a stage for testing substrate 118. The location of various metrology pads 122 on substrate 118 are preprogrammed into computer 32. The computer then directs movement of the substrate support 60 to place the metrology pad 122 beneath the analyzing beam location. However, because the substrate may be misplaced on the support resulting in the substrate being "off centered" the exact location of the metrology pads may not be known. Additionally, movement of the robotic stage may be somewhat unpredictable and imprecise adding further difficulty because the exact position of the substrate may not be known. Accordingly, the preprogrammed locations of the metrology pads may not accurately place the metrology pads directly or precisely beneath the x-ray beam. Accordingly, in embodiments of the present invention, the viewing system along with pattern recognition software may be used to move the substrate support and therefore the metrology pad closer to its proper location. In an embodiment of the present invention, once the metrology pad is moved closer to the proper location the e-beam 126 can be precisely steered on the anode and accurately locate the x-ray beam directly over the metrology pad to be tested. In an embodiment of the present invention, the robot and viewing system are used to move the metrology pads to be tested to within about 10-50 microns of the proper location and then the e-beam 126 shaped and moved to locate the x-ray beam 127 precisely over the metrology pad. In this way, a somewhat imprecise robot can be used to provide a perfectly precise stage for placing substrate metrology areas under the x-ray beam 127.

Figure 10A:
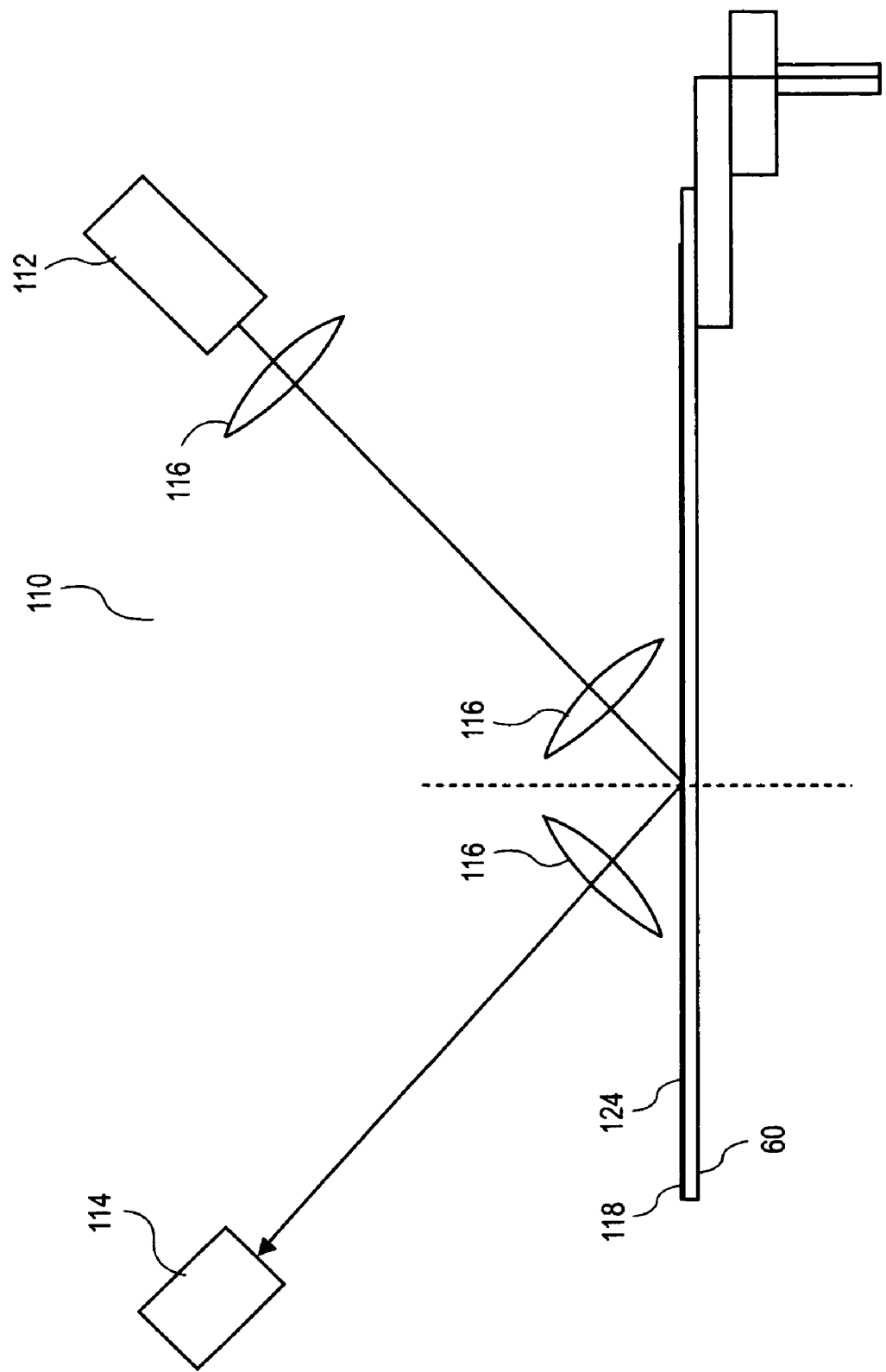
FIGS. 10A-10C are cross-sectional side schematic views of the metrology chamber illustrated in FIG. 1.
Figure 10B:
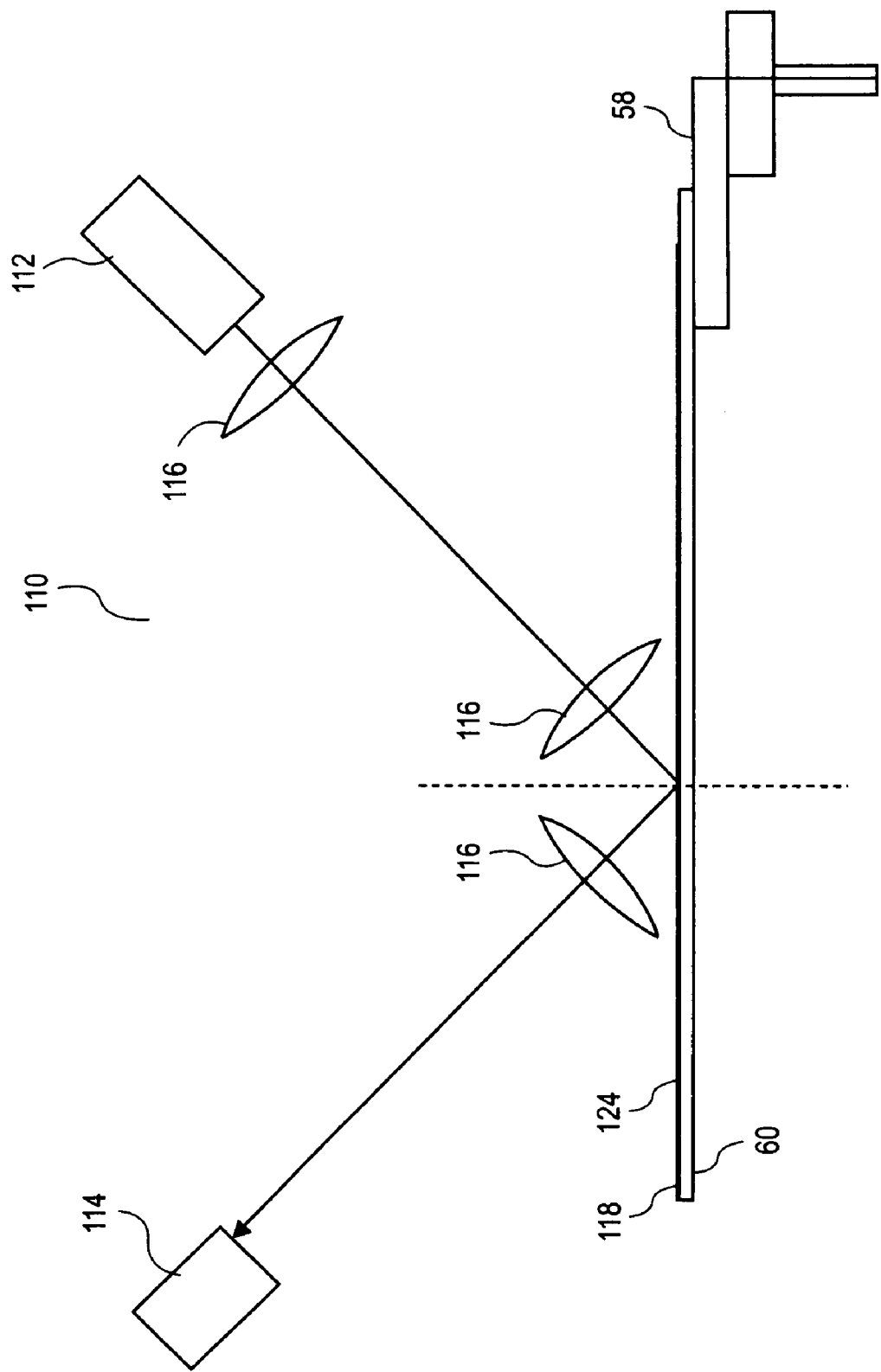
Figure 10C:
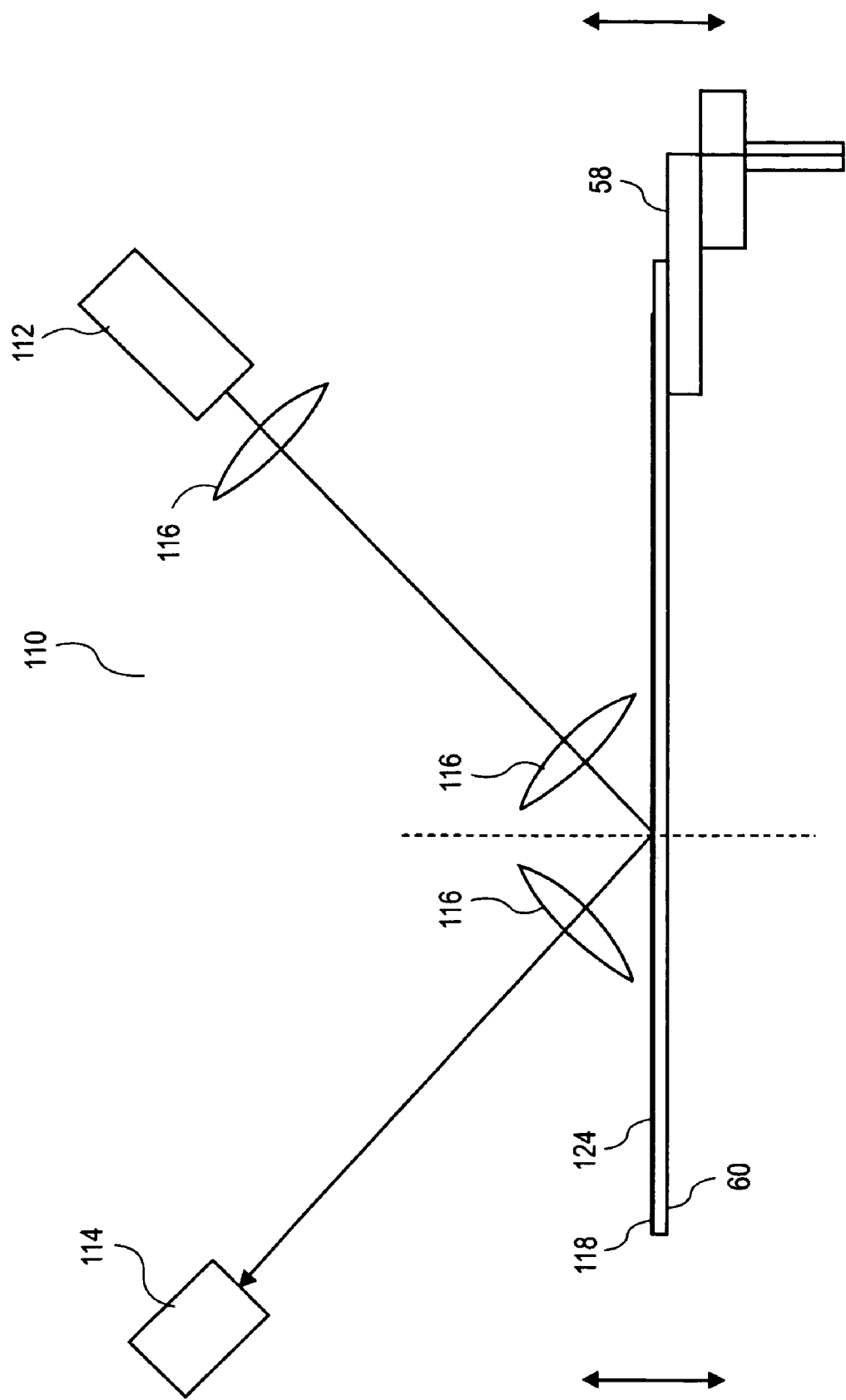

FIGS. 10A-10C illustrate the correction of the height of the substrate 118 relative the viewing subsystem 44 and the electromagnetic radiation source subsystem 42 illustrated in FIG. 1B. As shown in FIG. 10A, the laser 112 may direct a beam of laser light through the array of lenses 116 off of the upper surface of the substrate 118. The laser light may then strike and be detected by a laser detector 114. As illustrated in FIG. 10B, as the robotic arm 58 moves the substrate 118 between various positions within the metrology chamber 30, due to imperfections of the movement of the robotic arm, as well as imperfections of the substrate 118, such as variations in thickness and changes to the height of the upper surface 124 due to bowing or warping, the laser light that is reflected from the upper surface 124 of the substrate 118 may not enter the laser detector 114 at the same location.

Thus, the laser detector, in combination with the computer control console illustrated in FIG. 1A, may be able to detect variations in the height of the upper surface 124 of the substrate 118. As illustrated in FIG. 10C, the robotic arm 58 may then adjust the height of the substrate support 60, and thus the upper surface 124 of the substrate 118 to maintain a constant distance from the other components within the metrology chamber 30 as illustrated in FIG. 1B. Additionally, as illustrated in FIG. 4, anode 68 is connected to a stage, which enables anode 68 to be moved in a xy plane as well as in a vertical direction (z direction). The height detector subsystem 210 enables the height of anode 68 to be precisely. The height detector subsystem 210 includes a laser beam 212 and an array of lens 216 to shine a laser light onto the upper surface of anode 68. The laser light may then be detected by a laser detector 214. The laser and detector enable the anode height to be precisely measured and controlled.

The ability to precisely control the anode in the vertical direction (z direction) allows the surface of the anode to be precisely located at a focal point of the monochromator even when the anode surface may be nonplanar. In this way, the anode may be moved in the xy plane, and any nonplanarity in the anode surface compensated for by adjusting the anode height. Similarly, the ability to precisely control the substrate support in the vertical direction (z direction), allows the surface of the substrate to be precisely located at a focal point of the monochromator even when the height of the substrate surface may vary due to substrate nonplanarity, warpage or robot imprecision.

One advantage is that the robotic stage may be used to retrieve substrates from the load-lock chamber, as well as position the substrates under the electromagnetic radiation source subsystem. Therefore, a separate machine is not needed to remove the substrates from the load-lock chamber, which reduces the cost of the metrology tool.

Another advantage is that because a single machine is used to remove the substrates from the load-lock chamber and position them into the test position, when in the test position, the space immediately below the substrate support may be vacant of any hardware necessarily for the movements of the substrate. Therefore, the magnetic lens may be positioned more closely to the substrate support, which increases the effectiveness of the magnetic field generated by the magnetic lens in guiding the electrons from the substrate into the metrological analyzer and/or reduces the strength of the magnetic field that is necessary to effectively guide the electrons into the metrological analyzer.

A further advantage is that the portion of the substrate that is being tested may be viewed by the viewing subsystem in a direction that is normal to the upper surface of the substrate. Additionally, the portion of a substrate that has been tested may be viewed while the testing is taking place.

A further advantage is that because the magnetic lens is located outside of the vacuum chamber, any repairs required on the magnetic lens may be performed without exposing the contents of the metrology chamber to outside air. Therefore, the likelihood of any contamination within the metrology chamber is reduced. A further advantage is that the viewing subsystem contains no moving parts.

Other embodiments may utilize only certain aspects of the system described above. For example, the magnetic lens described as being positioned outside of the vacuum chamber may be used without the particular viewing system described.

While certain exemplary embodiments have been described and shown in the accompanying drawings, it is to be understood that such embodiments are merely illustrative and not restrictive of the current invention, and that this invention is now restricted to the specific constructions and arrangements shown and described since modifications may occur to those ordinarily skilled in the art.

What is claimed:

1. A photoelectron spectroscopy system comprising:
   a chamber wall enclosing a chamber;
   a substrate support positioned within the chamber to support a semiconductor substrate;
   an electromagnetic radiation source to emit electromagnetic radiation onto the substrate on the substrate support, the electromagnetic radiation causing photoelectrons to be emitted from the substrate;
   an analyzer to capture the photoelectrons emitted from the material on the substrate; and
   a magnetic field generator to generate a magnetic field within the chamber and guide the photoelectrons from the substrate to the analyzer wherein the analyzer and the magnetic field generator are positioned on opposing sides of the substrate support.

2. The system of claim 1, wherein the magnetic field generator is positioned beneath the substrate support.

3. The system of claim 2, wherein the chamber comprises a first portion and a second portion.

4. The system of claim 3, further comprising:
   a load-lock chamber adjacent to the first portion of the chamber; and
   a robotic stage having a base and a robotic arm, the substrate support being attached to the robotic arm, the arm being rotatably connected to the base, the base being connected to the chamber wall.

5. The system of claim 4, wherein when the substrate support is in the second portion of the chamber, the analyzer and the magnetic field generator are positioned on opposing sides of the substrate support.

6. The system of claim 5, wherein when the substrate support is in the second portion of the chamber, the magnetic field generator is positioned beneath the substrate support.

7. The system of claim 6, wherein the chamber is a vacuum chamber and the magnetic field generator is not positioned within the vacuum chamber.

8. A photoelectron spectroscopy system comprising:
   a chamber wall enclosing a vacuum chamber;
   a substrate support positioned within the vacuum chamber to support a substrate;
   an electromagnetic radiation source to emit electromagnetic radiation onto the substrate on the substrate support, the electromagnetic radiation causing photoelectrons to be emitted from the substrate;
   an analyzer to capture the photoelectrons emitted from the substrate; and
   a magnetic field generator to generate a magnetic field within the vacuum chamber and guide the photoelectrons from the substrate to the analyzer, the magnetic field generator being positioned outside of the vacuum chamber.

9. The system of claim 8, wherein the analyzer and the magnetic field generator are positioned on opposing sides of the substrate support.

10. The system of claim 9, wherein the magnetic field generator is positioned beneath the substrate support.

11. The system of claim 8, wherein the chamber comprises a first portion and a second portion.

12. The system of claim 11, further comprising:
    a load-lock chamber adjacent to the first portion of the chamber; and
    a robotic stage having a base and a robotic arm, substrate support being attached to the robotic arm, the robotic arm being rotatably connected to the base to transport the substrate support from the load-lock chamber to the second portion of the chamber.

13. The system of claim 12, wherein when the substrate support is in the second portion of the chamber, the analyzer and the magnetic field generator are positioned on opposing sides of the substrate support.

14. The system of claim 13, wherein when the substrate support is in the second portion of the chamber, the magnetic field generator is positioned beneath the substrate support.

15. A photoelectron spectroscopy system comprising:
a chamber wall enclosing a chamber having a loading portion and a testing portion;
a robotic stage having a robotic arm and a substrate support, the robotic arm being capable of moving the substrate support between the loading and testing portions of the chamber;
an electromagnetic radiation source to emit electromagnetic radiation onto a substrate on the substrate support when the substrate support is in the testing portion of the chamber, the electromagnetic radiation causing photoelectrons to be emitted from a material of the substrate;
an analyzer to capture the photoelectrons emitted from the substrate; and
a magnetic field generator to generate a magnetic field within the chamber and guide the photoelectrons from the substrate to the analyzer, the magnetic field generator being positioned beneath the substrate support when the substrate support is in the testing portion of the chamber.

16. The system of claim 15, wherein the chamber is a vacuum chamber and the magnetic lens is not positioned within the vacuum chamber.

17. The system of claim 16, wherein the magnetic lens is less than 5 mm beneath the substrate support when the substrate support is in the testing portion of the chamber.

18. The system of claim 17, wherein at least a portion of the robotic arm rotates about an axis of rotation, the axis of rotation passing through the entry portion of the chamber.

19. A photoelectron spectroscopy system comprising:
a chamber wall enclosing a chamber;
a substrate support positioned within the chamber to support a substrate;
an electromagnetic radiation source to emit electromagnetic radiation onto a portion of the substrate on the substrate support, the electromagnetic radiation causing photoelectrons to be emitted from the substrate;
an analyzer to capture the photoelectrons emitted from the portion of the substrate; and
a camera subsystem to collect visible light that is reflected off the portion of the substrate and capture an image of the portion of the substrate.

20. The system of claim 19, wherein the visible light propagates from the portion of the substrate perpendicularly to an upper surface of the substrate.

21. The system of claim 19, wherein the photoelectrons captured by the analyzer are emitted from the portion of the substrate in a first direction and the visible light collected by the camera subsystem propagates from the portion of the substrate in a second direction, the first and second directions being substantially parallel.

22. The system of claim 21, wherein the photoelectrons captured by the analyzer and the visible light collected by the camera subsystem at least partially intersect.

23. The system of claim 22, wherein the photoelectrons captured by the analyzer are arranged in a photoelectron bundle having a central axis, the visible light collected by the camera subsystem is arranged in a visible light bundle having a central axis, and the central axis of the photoelectron bundle is coaxial with the central axis of the visible light bundle.

24. The system of claim 23, wherein the camera subsystem further comprises a camera and a reflector, the reflector being positioned above the portion of the substrate and having a reflective surface and an opening therethrough, the photoelectrons passing through the opening and into the analyzer and the visible light being reflected off the reflective surface and into the camera.

25. The system of claim 24, wherein the reflector is positioned between the analyzer and the substrate support.

26. The system of claim 25, wherein the chamber comprises a first portion and a second portion.

27. The system of claim 26, further comprising:
a load-lock chamber coupled to the first portion of the chamber; and
a robotic stage having a base and a robotic arm, the substrate support being attached to the robotic arm, the robotic arm being rotatably connected to the base to transport the substrate support from the load-lock chamber to the second portion of the chamber.

28. The system of claim 27, further comprising a magnetic field generator to generate a magnetic field within the chamber and guide the photoelectrons from the substrate to the analyzer.

29. The system of claim 28, wherein when the substrate support is in the second portion of the chamber, the analyzer and the magnetic field generator are positioned on opposing sides of the substrate support.

30. The system of claim 29, wherein the magnetic field generator creates a magnetic field which has a rotational symmetry which is coaxial with the central axes of the photoelectron bundle and the visible light bundle.

31. The system of claim 24, wherein the camera and the reflector are connected to the chamber wall in fixed positions relative to each other.

32. The system of claim 31, wherein the camera and the reflector are connected to the chamber wall in fixed positions.

33. A photoelectron spectroscopy system comprising:
a chamber wall enclosing a chamber;
a substrate support positioned within the chamber to support a substrate;
an electromagnetic radiation source to emit electromagnetic radiation onto a portion of the substrate on the substrate support, the electromagnetic radiation causing photoelectrons to be emitted from the portion of the substrate;
an analyzer to capture the photoelectrons emitted from the portion of the substrate;
a magnetic field generator to generate a magnetic field within the chamber and guide the photoelectrons from the substrate to the analyzer; and
a camera subsystem to collect visible light that is reflected off the portion of the substrate and capture an image of the portion of the substrate.

34. The system of claim 33, wherein the visible light propagates from the portion of the substrate perpendicularly to an upper surface of the substrate.

35. The system of claim 33, wherein the photoelectrons captured by the analyzer are emitted from the portion of the substrate in a first direction and the visible light collected by the camera subsystem propagates from the portion of the substrate in a second direction, the first and second directions being substantially parallel.

36. The system of claim 35, wherein the photoelectrons captured by the analyzer and the visible light collected by the camera subsystem at least partially intersect.

37. The system of claim 36, wherein the photoelectrons captured by the analyzer are arranged in a photoelectron bundle having a central axis, the visible light collected by the camera subsystem is arranged in a visible light bundle having a central axis, and the central axis of the photoelectron bundle is coaxial with the central axis of the visible light bundle.

38. The system of claim 37, wherein the magnetic field generator creates a magnetic field which has rotational symmetry which is coaxial with the central axes of the photoelectron bundle and the visible light bundle.

39. The system of claim 38, wherein the camera subsystem further comprises a camera and a reflector, the reflector being positioned above the portion of the substrate and having a reflective surface and an opening therethrough, the photoelectrons passing through the opening and into the analyzer and the visible light being reflected off the reflective surface and into the camera.

40. The system of claim 39, wherein the reflector is positioned between the analyzer and the substrate support.

41. The system of claim 40, wherein the chamber comprises a first portion and a second portion.

42. The system of claim 41, further comprising:
a load-lock chamber connected to the frame and being adjacent to the first portion of the chamber; and
a robotic stage having a base and a robotic arm, the substrate support being attached to the robotic arm, the robotic arm being rotatably connected to the base to transport the substrate support from the load-lock chamber to the second portion of the chamber.

43. The system of claim 42, wherein when the substrate support is in the second portion of the chamber, the analyzer and the magnetic field generator are positioned on opposing sides of the substrate support.

44. The system of claim 43, wherein the camera and the reflector are connected to the chamber wall in fixed positions relative to each other.

45. The system of claim 44, wherein the camera and the reflector are connected to the chamber wall in fixed positions relative to the frame.

46. A photoelectron spectroscopy system comprising:
a substrate support to support a substrate having an upper surface; and
a camera subsystem to collect visible light that is reflected off a portion of the substrate and capture an image of the portion of the substrate, the visible light propagating from the portion of the substrate in a direction that is substantially perpendicular to the upper surface of the substrate upper surface.

47. The system of claim 46, wherein the camera subsystem further comprises a camera and a reflector, the reflector being positioned above the portion of the substrate and having a reflective surface and an opening therethrough.

48. The system of claim 47, wherein the camera and the reflector are connected in fixed positions relative to each other.

49. The system of claim 48, wherein the camera and the reflector are connected to a chamber wall enclosing a chamber wherein said substrate support is in said chamber.

50. The system of claim 49, wherein reflector is positioned above the substrate and the substrate support is capable of moving the substrate towards and away from the camera subsystem.

51. A photoelectron spectroscopy system comprising:
a substrate support to support a substrate;
an anode;
an electron gun to direct a beam of electrons onto said anode, said electrons causing an electromagnetic radiation to be emitted from said anode;
a beam shaper for shaping said beam of electrons into a first beam shape on a first portion of said anode and into a second beam shape onto a second portion of said anode; and
a monochromator to redirect the electromagnetic radiation emitted from said anode onto said substrate, wherein when the first beam shape of electrons is directed onto the said first portion of said anode, the electromagnetic radiation striking a first target portion of said substrate with said first beam shape, and wherein said second beam of electrons is directed onto said second portion of said anode, the electromagnetic radiation striking a second target portion of said substrate with said second beam shape.

52. The system of claim 51, wherein said first beam shape is an elongated oval or rectangle.

53. The system of claim 52, wherein said elongated oval or rectangle has a length and a width wherein the length is at least twice the width.

54. The system of claim 51, wherein said first beam shape and said second beam shape are both elongated ovals or rectangles.

55. The system of claim 51, wherein the second portion of the anode at least partially overlaps the first portion of the anode.

56. The systems of claim 51, wherein said first beam shape on said first portion of said anode is rotated to said second portion of said anode to form said second beam shape.

57. The system of claim 56, wherein said substrate support is coupled to a robot which moves said substrate support in a polar (R, Ø) coordinate system.

58. The system of claim 51, wherein said beam of electrons has a power rating of greater than 100 watts.

59. The system of claim 52, wherein said first shape has an area of between 400 and 40,000 microns$^2$.

60. A method of conducting photoelectron spectroscopy comprising:
placing a substrate having a metrology pad on a substrate support wherein said substrate support is connected to a robot;
moving said substrate support to a test location; and
generating an electromagnetic radiation beam and shaping said electromagnetic radiation beam to position said electromagnetic radiation beam over said metrology pad of said substrate; and
shaping said electromagnetic radiation into a second beam shape to place said second beam of electromagnetic radiation over a second metrology pad of said substrate.

61. The method of claim 60, wherein said robot moves said substrate support to said test location utilizing preprogrammed coordinates.

62. The method of claim 60, wherein said robot moves said substrate support utilizing polar coordinates (R, Ø).

63. The method of claim 60, further comprising after moving said substrate support to said test location, utilizing an optical viewing system to determine the location of said metrology pad.

64. The method of claim 60, wherein said viewing system receives light reflected from said metrology pad centered around a direction perpendicular to said substrate.

65. The method of claim 60, further comprising moving said substrate support to a second test location wherein moving said substrate support from said first test location to said second test location includes rotating said substrate support.

* * * * *